US006692603B1

(12) United States Patent
Lindsay et al.

(10) Patent No.: US 6,692,603 B1
(45) Date of Patent: Feb. 17, 2004

(54) METHOD OF MAKING MOLDED CELLULOSIC WEBS FOR USE IN ABSORBENT ARTICLES

(75) Inventors: Jeffrey Dean Lindsay, Appleton, WI (US); Fung-jou Chen, Appleton, WI (US); Robert Eugene Vogt, Neenah, WI (US); Julie Marie Bednarz, Neenah, WI (US); Tong Sun, Neenah, WI (US); Kambiz Bayat Makoui, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/684,039

(22) Filed: Oct. 6, 2000

Related U.S. Application Data

(60) Provisional application No. 60/159,629, filed on Oct. 14, 1999.

(51) Int. Cl.$^7$ .............................. B31F 1/07; A61F 13/15
(52) U.S. Cl. .................. 156/209; 156/242; 156/244.17; 156/245; 156/272.2; 264/257; 604/366; 604/374; 604/385.01
(58) Field of Search ................................ 156/196, 199, 156/209, 242, 244.17, 245, 272.2, 273.7, 275.7, 321; 264/405, 484, 489, 491, 239, 257; 604/365, 366, 367, 374, 385.01; 19/301

(56) References Cited

U.S. PATENT DOCUMENTS

| 3,442,268 A | 5/1969 | Bird |
| 3,700,623 A | 10/1972 | Keim |
| 3,825,381 A | 7/1974 | Dunning et al. |
| 3,855,158 A | 12/1974 | Petrovich et al. |
| 3,920,015 A | 11/1975 | Wortham |

(List continued on next page.)

FOREIGN PATENT DOCUMENTS

| DE | 297 03 589 U1 | 7/1997 |
| EP | 0 638 303 B1 | 2/1995 |
| EP | 0 665 315 B1 | 8/1995 |
| EP | 0 985 741 A1 | 9/1998 |
| GB | 2 319 186 A | 11/1997 |
| JP | 04146748 | 5/1992 |
| WO | WO 88/01494 | 3/1988 |
| WO | WO 92/17643 | 10/1992 |
| WO | WO 94/16658 | 8/1994 |
| WO | 96/00625 | 1/1996 |

(List continued on next page.)

OTHER PUBLICATIONS

American Society for Testing Materials (ASTM) Designation: D 4032–82, "Standard Test Method for Stiffness of Fabric by the Circular Bend Procedure," pp. 702–706, published Aug. 1982.
Haile et al., "Copolyester Polymer for Binder Fibers", Nonwovens World, Apr.–May 1999, pp. 120–124.
R.C. Metaxas & R.J. Meredith, "Industrial Microwave Heating", Peter Peregrinus, LTD, London, 1983, pp. 183–195; pp. 288–289.

Primary Examiner—Michael W. Ball
Assistant Examiner—John T. Haran
(74) Attorney, Agent, or Firm—Pauley Petersen & Erickson

(57) ABSTRACT

Methods are disclosed for producing absorbent articles comprising molded airlaid webs and other molded fibrous webs. The molded webs can offer improved body fit and/or improved fluid handling. Molded airlaid webs, for example, can be formed having a central longitudinal hump and flexure zones longitudinally removed from the central hump to provide good contact with the body and improved fit when the article is squeezed from the sides. Molding can be achieved when a binder material is activated by an energy source and the web is held against a molding substrate. Energy sources can include microwaves, heated air, heated metal surfaces, ultraviolet radiation, ultrasonic energy, and the like.

45 Claims, 14 Drawing Sheets

U.S. PATENT DOCUMENTS

| | | |
|---|---|---|
| 4,100,324 A | 7/1978 | Anderson et al. |
| 4,234,775 A | 11/1980 | Wolfberg et al. |
| 4,285,343 A | 8/1981 | McNair |
| 4,342,314 A | 8/1982 | Radel et al. |
| 4,397,644 A | 8/1983 | Matthews et al. |
| 4,463,045 A | 7/1984 | Ahr et al. |
| 4,476,180 A | 10/1984 | Wnuk |
| 4,478,853 A | 10/1984 | Chaussee |
| 4,578,133 A | 3/1986 | Oshefsky et al. |
| 4,608,047 A | 8/1986 | Mattingly |
| 4,617,124 A | 10/1986 | Pall et al. |
| 4,622,089 A | 11/1986 | Lauritzen |
| 4,678,464 A | 7/1987 | Holtman |
| 4,687,478 A | 8/1987 | Van Tilburg |
| 4,740,409 A | 4/1988 | Lefkowitz |
| 4,758,240 A | 7/1988 | Glassman |
| 4,820,307 A | 4/1989 | Welch et al. |
| 4,879,170 A | 11/1989 | Radwanski et al. |
| 4,897,499 A | 1/1990 | Hutton et al. |
| 4,904,249 A | 2/1990 | Miller et al. |
| 3,860,003 | 6/1990 | Buell |
| 4,950,264 A | 8/1990 | Osborn, III |
| 5,009,653 A | 4/1991 | Osborn, III |
| 5,042,986 A | 8/1991 | Kitchens et al. |
| 5,057,368 A | 10/1991 | Largman et al. |
| 5,069,970 A | 12/1991 | Largman et al. |
| 5,108,691 A | 4/1992 | Elliott |
| 5,108,820 A | 4/1992 | Kaneko et al. |
| 5,151,092 A | 9/1992 | Buell et al. |
| 5,167,771 A | 12/1992 | Sayers et al. |
| 5,169,571 A | 12/1992 | Buckley |
| 4,589,876 A | 4/1993 | Van Tilburg |
| 5,228,947 A | 7/1993 | Churchland |
| 5,267,992 A | 12/1993 | Van Tilburg |
| 5,277,976 A | 1/1994 | Hogle et al. |
| 5,308,346 A | 5/1994 | Sneller et al. |
| 5,336,552 A | 8/1994 | Strack et al. |
| 5,338,169 A | 8/1994 | Buckley |
| 5,342,342 A | 8/1994 | Kitaoka |
| 5,350,624 A | 9/1994 | Georger et al. |
| 5,382,400 A | 1/1995 | Pike et al. |
| 5,399,412 A | 3/1995 | Sudall et al. |
| 5,429,686 A | 7/1995 | Chiu et al. |
| 5,533,991 A | 7/1996 | Kirby et al. |
| 5,536,921 A | 7/1996 | Hedrick et al. |
| 5,545,156 A | 8/1996 | DiPalma et al. |
| 5,560,793 A | 10/1996 | Ruscher et al. |
| 5,591,298 A | 1/1997 | Goodman et al. |
| 5,609,727 A | 3/1997 | Hansen et al. |
| 5,611,790 A | 3/1997 | Osborn, III et al. |
| 5,620,779 A | 4/1997 | Levy et al. |
| 5,624,423 A | 4/1997 | Anjur et al. |
| 5,649,916 A | 7/1997 | DiPalma et al. |
| 5,650,218 A | 7/1997 | Krzysik et al. |
| 5,656,111 A | 8/1997 | Dilnik et al. |
| 5,665,396 A | 9/1997 | Ulman |
| 5,692,939 A | 12/1997 | DesMarais |
| 5,725,821 A | 3/1998 | Gannon et al. |
| 5,807,365 A | 9/1998 | Luceri |
| 5,833,679 A * | 11/1998 | Wada ........................ 604/384 |
| 5,849,000 A | 12/1998 | Anjur et al. |
| 5,858,512 A | 1/1999 | Dit Picard et al. |
| 5,871,763 A | 2/1999 | Luu et al. |
| 5,906,879 A | 5/1999 | Huntoon et al. |
| 5,916,203 A | 6/1999 | Brandon et al. |
| 5,916,678 A | 6/1999 | Jackson et al. |
| 5,938,995 A | 8/1999 | Koltisko, Jr. et al. |
| 5,948,710 A | 9/1999 | Pomplun et al. |
| 5,958,275 A | 9/1999 | Joines et al. |
| 5,962,112 A | 10/1999 | Haynes et al. |
| 5,968,430 A | 10/1999 | Naito et al. |
| 5,990,377 A | 11/1999 | Chen et al. |
| 6,000,102 A | 12/1999 | Lychou |
| 6,001,300 A | 12/1999 | Buckley |
| 6,020,580 A | 2/2000 | Lewis et al. |
| 6,080,691 A | 6/2000 | Lindsay et al. |
| 6,085,437 A | 7/2000 | Stipp |
| 6,098,249 A | 8/2000 | Toney et al. |
| 6,120,783 A | 9/2000 | Roe et al. |
| 6,171,682 B1 | 1/2001 | Raidel et al. |
| 6,191,340 B1 | 2/2001 | Carlucci et al. |
| 6,264,791 B1 | 7/2001 | Sun et al. |
| 6,326,525 B1 | 12/2001 | Hamajim et al. |
| 6,486,379 B1 * | 11/2002 | Chen et al. ................. 604/378 |
| 2002/0032421 | * 3/2002 | Scott et al. ................. 604/367 |

FOREIGN PATENT DOCUMENTS

| | | |
|---|---|---|
| WO | WO 96/07376 | 3/1996 |
| WO | WO 98/22060 | 5/1998 |
| WO | WO 98/22064 | 5/1998 |
| WO | WO 98/47455 | 10/1998 |
| WO | WO 99/00093 | 1/1999 |
| WO | WO 99/22686 | 5/1999 |
| WO | WO 99/61518 | 12/1999 |
| WO | WO 00/19955 | 4/2000 |
| WO | WO 00/19956 | 4/2000 |
| WO | WO 00/38747 | 7/2000 |
| WO | WO 00/62730 | 10/2000 |
| ZA | 98/4033 | 5/1998 |

* cited by examiner

METHOD OF MAKING MOLDED CELLULOSIC WEBS FOR USE IN ABSORBENT ARTICLES

This application claims priority to the provisional application Ser. No. 60/159,629, "Shaped Airlaid Layers for Personal Care Articles ("SLICK" Concept)," filed Oct. 14, 1999.

SUMMARY OF THE INVENTION

It has been discovered that airlaid webs comprising heat-sensitive binder material (thermoplastic or thermally curable) can be molded into useful, three-dimensional shapes providing improved body fit and flow control by means of an online process in which a flat airlaid web comprising binder material is held against a molding substrate after or during application of energy to the web, causing the web to conform to the molding substrate and form bonds that lock the web into the shape of the molding substrate. The web can be held against the molding substrate by pneumatic forces, tension in the web itself, tension applied by a belt or wire, restraining forces from a backing surface such as a second surface that conforms to the molding substrate, and the like. The molding substrate can be metal (e.g., aluminum, steel, copper, brass, titanium, and the like), glass, ceramic, plastic, a composite material, and the like, and can be gas permeable or impermeable.

The methods of the present invention can enable production at industrial speeds of molded absorbent structures shaped to provide both body fit and flow control in absorbent articles.

Molded airlaid structures within the scope of the present invention include those having slotted vertical gaps that offer an entranceway for gushes of body fluids, as well as anatomically conforming shapes adapted to not only receive and direct flowing fluids, but to also guide the flexure of the article in use to better conform to the body. Articles according to the latter concept can, for example, have a central elongated hump, one or more longitudinal flow channels, and a plurality of transverse flexure zones (hereafter described) away from the central hump to cause the article to flex toward the body when compressed from the sides. Such articles can adapt to fit the body of the wearer during the dynamic conditions of use, thereby providing both comfort and leakage prevention.

The energy can be applied by microwave radiation, radiofrequency energy, or other electromagnetic radiation sources, as well as by heated air or by conduction with heated surfaces. When microwave energy is applied, the web can incorporate binder materials such as thermoplastic binder fibers or curable resins that are relatively sensitive to microwave radiation (compared to pure cellulose itself) by virtue of a high dipole moment. In one embodiment, microwave energy is applied to the moving web as it passes through an opening in a microwave resonance chamber, where microwave energy is focused into the web. In another embodiment, microwave energy is applied to the web through a rotating microwave horn terminating in a microwave-transparent window having a three-dimensional structure suitable for molding the web. The rotating horn moves with the web while the web is near or in contact with the horn. A wide variety of other embodiments are also within the scope of the present invention, as set forth hereafter.

Alternatively, the energy can be applied in the form of heated gas passing through the web, or by conduction from one or more heated molding surfaces, or by application of ultrasonic energy, infrared energy, and the like. The energy heats the binder material, promoting fusion of a portion of the binder material to join fibers in the airlaid in the case of a thermoplastic binder, or promoting curing in the case of thermosetting materials or heat-curable crosslinking agents. The resulting molded airlaid web can be cut into discrete sections suitable for incorporation into an absorbent article. The section of airlaid web can have any one or more of the following characteristics: a substantially uniform density, an apparent thickness at least 50% greater than the original thickness of the unmolded web, an Overall Surface Depth (hereafter defined) of at least 0.5 mm, a Surface Height of at least 1 mm, a wet compressed bulk at least 50% greater than that of the unmolded web, a longitudinally elongated central hump and one or more transverse flexure zones between the hump and one or more of the longitudinal ends of the section of the airlaid web, and one or more longitudinal flow channels formed by elevated structures on the section of the airlaid web.

As used herein, an "airlaid web" is a fibrous structure formed primarily by a process involving deposition of air-entrained fibers onto a mat, typically with binder fibers present, and typically followed by densification and thermal bonding. In addition to traditional thermally bonded airlaid structures (those formed with non-tacky binder material present and substantial thermally bonded), the scope of the term "airlaid" according to the present invention can also include coform, which is produced by combining air-entrained dry, dispersed cellulosic fibers with meltblown synthetic polymer fibers while the polymer fibers are still tacky. Further, an airformed web to which binder material is subsequently added can be considered within the scope of the term "airlaid" according to the present invention. Binder can be added to an airformed web in liquid form (e.g., an aqueous solution or a melt) by spray nozzles, direction injection or impregnation, vacuum drawing, foam impregnation, and so forth. Solid binder particles can also be added by mechanical or pneumatic means.

As used herein, an "airformed web" refers to a mat comprising cellulosic fibers such as those from fluff pulp that have been separated, such as by a hammermilling process, and then deposited on a porous surface without a substantial quantity of binder fibers present. Airfelt materials used as the absorbent core in many diapers, for example, are a typical example of an airformed material.

In one embodiment, the absorbent article of the present invention has an upper absorbent layer comprising a three-dimensional molded cellulosic airlaid web having a portion of water-resistant thermoplastic binder material therein. The molded airlaid web can have a substantially uniform basis weight and thickness prior to molding, but is molded to have a plurality of elevated regions offering a distinctive profile well suited for conforming to the body of the wearer. The molded web can also be adapted for providing significant void volume beneath the upper absorbent layer and preventing leakage to the sides of the article. In some embodiments, the molded airlaid web has a body-side surface topography comprising a central hump having an oval shape elongated in the longitudinal direction, and a plurality of molded flexure zones having a component extending in the transverse direction and disposed between the central hump and at least one longitudinal end of the molded airlaid web. The molded flexure zones assist in permitting an initially flat article to readily conform to the shape of the wearer's body along the longitudinal axis of the article.

In one embodiment, thermal molding is achieved as hot gas passes through the web in the region to be molded, causing the binder material to become activated (e.g., for thermoplastic material such as binder fibers to at least partially melt and bond cellulosic fibers together) to hold the web in the shape defined by the mold. Heat transfer may further be assisted by providing an oscillatory flow of heated gas with a reverse flow component, such as is found in the heated gases produced from pulsed combustion systems, wherein acoustic waves enhance the heat transfer of the gases. An exemplary system for providing oscillatory flow of heated gases suitable for the present invention is disclosed in U.S. Pat. No. 6,085,437, issued Jul. 1, 1998 to G. K. Stipp, herein incorporated by reference.

When shaping of the web comprises application of mechanical pressure from a solid surface, as opposed to pneumatic pressure, the web can be heated before the mechanical forces for shaping are fully applied in order reduce damage to the web and achieve higher strength and molding definition. Such preheating can be achieved with any known method, such as steam impregnation, heated air passing through the web, application of radiative or radiofrequency energy, and the like. Alternatively, the solid surfaces themselves may be heated to cause heating of the web sufficient to activate the binder material.

While webs can be heated by conduction, high-bulk cellulosic webs can be poor conductors and may not always permit uniform treatment of the web under the constraint of short heating times. Other forms of heat can be applied as the web is being held in a desired shape. Suitable forms include application of ultrasonic energy; radiofrequency energy such as microwaves, particularly when binder material in the airlaid web is responsive to such radiofrequency energy; and convective heating from hot gases passing through or impinging onto the web.

For many binder materials, heating to temperatures above about 90° C. is required for effective activation of the binder material. For example, many thermoplastic binder materials become activated over a temperature range of about 95° C. to 200° C., more specifically from about 100° C. to about 170° C., and most specifically from about 110° C. to 150° C. The higher the temperature, the higher the molding definition. Excessive temperatures should be avoided to prevent scorching or other harm to the web.

Radiofrequency Heating (Microwaves)

The use of radiofrequency energy, microwaves or other electromagnetic means of applying energy to a web can allow more uniform treatment of the web or of any binder material in the web. As used herein, "radiofrequency" (RF) energy comprises electromagnetic radiation in the spectral range of 300 Hz to 300 GHz. "Microwave radiation" is a subset of RF radiation spanning the spectral range from 30 MHz to 300 GHz. Typical frequencies for microwave energy are 915 MHz and 2450 MHz (2.45 GHz), the ISM bands allowed by the Federal Communication Commission (FCC). General principles for microwave heating are given by R. C. Metaxas and R. J. Meredith in *Industrial Microwave Heating*, Peter Peregrinus, LTD, London, 1983. A useful tool in the design of microwave heating systems is the HFSS™ software provided by Ansoft Corp. (Pittsburgh, Pa.).

In one embodiment, applying sufficient energy to the airlaid web comprises application of microwaves to cause components in the web to heat sufficiently to fuse or melt thermoplastic binder materials. For example, an airlaid web can comprise fibers and/or particles of dipolar polymers such as polyurethanes, isocyanates, polyethylene oxide, polyester, and their derivatives, or mixtures or copolymers formed therefrom. Application of microwave radiation causes the dipolar polymers to become heated enough to either fuse or to cause other less dipolar thermoplastic materials to fuse. For example, a sheath-core bicomponent fiber with a polyester core and a polyolefin sheath can be subjected to microwave radiation to cause the core to heat sufficiently to cause melting of the sheath without melting or degradation of the core. Alternatively, the sheath can be more microwave susceptible than the core. An exemplary application of microwave energy is found in the commonly owned PCT publication WO 99/22686, "Composite Material with Elasticized Portions and a Method of Making the Same," by R. G. Brandon, F. M. Chen, and R. E. Vogt, U.S. Pat. No. 5,916,203, issued Jun. 29, 1999. Further details of providing microwave chambers for applying energy to a moving web are disclosed in U.S. Pat. No. 5,536,921, issued Jul. 16, 1996 to Hedrick et al.; U.S. Pat. No. 6020580; and U.S. Pat. No. 4,234,775, issued Nov. 18, 1980 to Wolfberg et al.; all of which are herein incorporated by reference.

U.S. Pat. No. 5,958,275, issued Sep. 28, 1999 to Joines et al., herein incorporated by reference, provides several useful embodiments for application of microwave energy to a moving planar material such as a web. The web passes through a slot in a microwave chamber that has adjustably variable path lengths to allow peaks and valleys of the electromagnetic field in one exposure segment to compensate for peaks and valleys in another exposure segment. For example, the microwave chamber may have a serpentine shape that makes several passes over the web to ensure uniform application of microwave energy. Specialized choke flanges prevent the escape of electromagnetic energy. One or more rollers between exposure segments in the microwave chamber may be enclosed by an outer surface to prevent the escape of electromagnetic energy.

In an embodiment related to the equipment disclosed in commonly owned U.S. application Ser. No. 09/603714 by R. E. Vogt, filed Jun. 27, 2000, herein incorporated by reference, microwave energy is directed by a waveguide into a resonance chamber adapted to focus energy into a plane or along a line through which the moving web passes. A cylindrical chamber can be suitable, for example, wherein the web travels along a diameter of the chamber, entering and leaving through slots along opposing sides of the cylinder. Quarter-wavelength chokes extend outward from the slots to prevent excess leakage of microwave radiation through the slots. When tuned for microwave energy to fill the chamber in the $TM_{010}$ mode, the energy is focussed along the axis of the cylinder and thus into the web for efficient delivery of energy. (TM modes are generally expected to be useful for microwave heating of a web in the present invention. TEM modes can be used but are more likely to permit leakage of microwaves from the chamber.) The web may be carried on a belt of material such as Teflon™ that is relatively unsusceptible to microwave energy, or the web can pass through the chamber without being on a carrier belt.

General principles for use of cylindrical resonance chambers for microwave heating and the coupling of a waveguide to an aperture in the cylinder are given by R. C. Metaxas and R. J. Meredith in *Industrial Microwave Heating*, Peter Peregrinus, LTD, London, 1983, pp. 183–195. In general, a rectangular waveguide is choked down through an aperture in the center of the cylinder (e.g., on the top or bottom of the central portion of the cylinder when a web runs through the middle of the cylinder along the horizontal diameter) to provide efficient transfer and distribution of microwave energy into the cylinder.

U.S. Pat. No. 6,020,580, issued Feb. 1, 2000 to Lewis et al., herein incorporated by reference, discloses a suitable microwave applicator with an elongated chamber such as a cylindrical shape which can be used or adapted in accordance with Vogt (U.S. application Ser. No. 09/603714) for use in the present invention. A waveguide, connected to the elongated chamber, couples microwave power into the elongated chamber. The cross-sectional area of the elongated chamber can be mechanically adjusted to control and maintain the microwave field uniformity and resonant mode, suitably a length independent mode $TM_{010}$, during the processing of the material. The applicator thus provides microwave energy having a substantially uniform field distribution over a large area for processing a web.

In addition to heating and activating thermoplastic binder materials, electromagnetic radiation in the form of microwaves or ultraviolet radiation, for example, can also be used to cure resins that are in liquid form. For example, an airlaid web can be impregnated or sprayed with a liquid binder system, followed by application of light pressure to mold the web into a three-dimensional shape as radiation is applied to cure the liquid binder. Heat can also be applied to cure some binder systems, wherein the heat is applied by through drying or other convective means with hot gas passing into the web, infrared radiation, conduction, and the like. Examples of microwave and UV curing of resins in a fibrous preform is found in U.S. Pat. No. 5,169,571, issued Dec. 08, 1992 to D. T. Buckley, and in U.S. Pat. No. 5,338,169, issued Aug. 16, 1994, also to Buckley, both of which are herein incorporated by reference. One form of convective heat transfer of value in the present invention is the hot air knife, or HAK, as described in U.S. Pat. No. 5,962,112, issued Oct. 5, 1999 to Haynes et al., herein incorporated by reference.

A method for simultaneously applying microwave radiation and applying moderate pressure to the web to mold it can be achieved by using a microwave-transparent solid material, or microwave window, as one of the surfaces pressing against a bulky web. Suitable microwave windows and cooling systems for the windows are disclosed in U.S. Pat. No. 5,228,947, "Microwave Curing System," issued Jul. 20, 1993 to M. T. Churchland, herein incorporated by reference in its entirety.

While the above examples typically are directed toward a web passing through stationary microwave equipment, the microwave energy or other energy sources for heating the web can be mounted to a moving structure (or energy from a stationary source can be guided into and distributed from a rotating device), such as a rotating wheel, or an moving belt or track, to move with the web for a predetermined length or time. A plurality of energy sources can be provided on the moving structure. A portion of the web can then be treated by a moving energy source, and upon separation from the energy source, the energy source can be repositioned to treat another portion of the moving web. For example, 10 or more microwave sources can move on an endless track, permitting five or more to be acting portions of the web at any time. In this manner the web can be molded by a moving molding substrate at the same time energy is applied to it.

By way of example, a moving web can rotate on a turret with a plurality of microwave horns, each terminating in a microwave-transparent window that can be pressed against the web as microwave energy is applied. The horns can be supplied with microwave energy from one or more stationary sources via a waveguide leading into the center of the rotating turret, or one or more microwave sources can be installed inside a rotating turret. The three-dimensional shape of the web as it is pressed against the microwave window can be locked into place by the fusion of binder material that joins fibers together once the binder material cools again. Alternatively, the binder material can be thermosetting or curable, becoming solidified or activated upon heating to hold the fibers together in the three-dimensional shape experienced during application of energy. A microwave-reflecting backing surface can be present, with the web residing between the backing surface and the microwave horn, to prevent microwave leakage and help establish effective resonance for heating of the web or the binder material therein.

When using microwave energy supplied radially outward from a turret, the web can be held against the molding substrate with a belt that can be microwave transparent or microwave reflecting, such as a belt with a metallic mesh therein.

U.S. Pat. No. 6,001,300, issued Dec. 14, 1999 to Buckley, herein incorporated by reference, also discloses methods for applying microwave energy into a three-dimensional mold through a molding surface transparent to microwave energy. Waveguides are used to uniformly distribute the energy. The microwave windows can comprise a plurality of segments to reduce the risk of cracking from thermal stress. The windows also can be configured as lenses to direct the microwave energy to desired portions of the article being treated, following principles disclosed in Buckley. For the present invention, the microwave window may be flat, in cooperative relationship with an opposing molding substrate, or it may be three-dimensional, in cooperative relationship with an opposing three-dimensional surface or a flat surface. For example, the microwave window may be a male molding surface matched with an opposing female surface which act together to impose a three-dimensional pattern to a web as microwave energy is applied to fuse a microwave-susceptible binder material to cellulosic fibers of the web. The resulting molded web can have a substantially uniform density, or can be molded to have two or more zones of differing density in a pattern.

Prior to application of microwave energy, the web may be provided with a small amount of moisture, particularly water comprising ions, to increase the susceptibility of the web to microwave radiation and/or to increase the moldability of the cellulosic fibers. For example, a water spray adding 2 to 10 weight percent of water to the web can be effective in improving the energy absorption of microwaves and/or the conformability of the web. Water can be added by gravure printing, nebulizers, atomizers, fine water jets, or other techniques, either uniformly to the web or to discrete zones in the web where more molding or heating is needed. The microwave energy applied may then dry off any undesired water add-on, or further drying by through-drying or other means can be applied.

Representative Binder Materials

Two classes of binder materials can be considered: thermoplastic solid materials (particles or fibers), and liquids (e.g., resins or solutions) that can be cured or set by application of heat or other energy sources to provide dry, water-resistant bonds between fibers. The binder material can comprise about 50% or less of the dry mass of the cellulosic web, such as from about 5% to 45%, or from 5% to 25%, or from 6% to 15%.

For solid binder materials, any known thermoplastic material can be used as a binder, provided that the material can be fused at a temperature that does not destroy or render unsuitable the fibrous mat itself. A thermoplastic binder upon activation by heat becomes soft but reverts to its normal frozen state upon cooling. Representative of such thermoplastic binder materials are polypropylenes, polyethylenes, polycarbonates, polyvinyl chloride, polyesters, polystyrenes, acrylics and the like. The binder material may be hydrophobic or hydrophilic. Hydrophilic fibers can be inherently hydrophilic or can be a synthetic hydrophobic fiber that has been treated with a hydrophilic coating. Examples of hydrophilic binder fibers are given in U.S. Pat. No. 5,849,000, issued Dec. 15, 1998 to Anjur et al., herein incorporated by reference.

The binder material can be unicomponent fibers or bicomponent polymer fibers such as sheath/core fibers or side-by-side bicomponent fiber, having a first component with a lower melting point than the second component, such that upon heating to about the melting point of the first component, the first component can fuse and bond to nearby cellulosic fibers while the second component can maintain the integrity of the binder fiber. Examples include DANAKLON® bicomponent fibers of Hercules, Inc. (Wilmington, Del.); or PET (poly(ethylene terphthalate)) core fibers an activated co-polyethylene sheath, such as CELBOND® fibers produced by KoSA Inc. (formerly Trevira Inc. and formerly Hoechst-Celanese), Salisbury, N.C., under the designation T-255 and T-256. Other useful binder fibers include the copolyester fibers described by W. Haile et al. in the article, "Copolyester Polymer for Binder Fibers," Nonwovens World, April–May 1999, pp. 120–124, or materials produced by ES FiberVisions Inc. (Wilmington, Del.). In addition to sheath/core fibers, components of a binder fiber having a plurality of polymers may be arranged in a side by side arrangement, a pie arrangement or an "islands-in-the-sea" arrangement, or in a blend. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. No. 5,277,976 to Hogle et al., and U.S. Pat. Nos. 5,069,970 and 5,057,368 to Largman et al., hereby incorporated by reference in their entirety, which describe fibers with unconventional shapes.

Unicomponent fibers can include, by way of example, polyethylene microfibers marketed as PULPEX™ fibers by Hercules, Inc. (Wilmington, Del.) or Eastman's Kodel® 410 binder fiber. This fiber requires a minimum temperature of about 132° C. for good bonding. CoPET B from Eastman Chemical Company is another commercially available binder material with an activation temperature of about 110° C. or higher. (This material can also be used as a sheath. For example, a useful bicomponent fiber is a coextruded sheath/core bicomponent with 35% CoPET B and a 65% PET core.) The binder material can also be a microwave-sensitize material having a high dielectric loss constant (e.g., from about 1 to 1,000 measured at a frequency of 1 kHz) such that the binder material is heated more than the cellulosic fibers when microwave energy is applied. (Cellulose can have a loss factor on the order of about 0.06 at 1 kHz.) Exemplary materials include polyamide or polyvinyl methyl based hot melt adhesives and other thermoplastics known in the art. Polyether block amides, polyvinylchloride (PVC) and related compounds also have high loss factors. The material can have a loss factor much greater than that of cellulose.

Binder materials can also be applied as liquid resins, slurries, colloidal suspensions, or solutions that become rigid or crosslinked upon application of energy (e.g., microwave energy, heat, ultraviolet radiation, electron beam radiation, and the like). For example, Stypol XP44-AB12-51B of Freeman Chemical Corp., a diluted version of the Freeman 44-7010 binder, is a microwave-sensitive binder that was used by Buckley et al. in U.S. Pat. No. 6,001,300, issued Dec. 14, 1999, previously incorporated by reference. Buckley et al. also disclose the following UV-sensitive binders available from Freeman Chemical: 80497 (slow system), 747-10 (medium system) and 19-4837 (fast system).

Various types of thermosetting binders are known to the art such as polyvinyl acetate, vinyl acetate, ethylene-vinyl chloride, styrene butadiene, polyvinyl alcohol, polyethers, and the like, as well as elastomeric latex emulsions. Representative thermosetting binder materials which are adapted for application in the form of a liquid dispersion include copolymers of ethylene and acrylic acid, vinyl acetate-ethylene copolymers, acrylonitrile-butadiene copolymers, vinylchloride polymers, vinylidene chloride polymers, curable acrylic latex compositions, "Airflex" available from Air Products & Chemicals, P.O. Box 97, Calvert City, Ky. 42029, and the like.

Latex that does not become crosslinked can be useful in producing an absorbent article that is also flushable after use. For example, commercial latex sources can be used, wherein a crosslinker is present, without causing significant crosslinking if the temperature of curing is kept below a designated temperature (e.g., below 130° C. for many latices), or if the pH is kept at a level incompatible with latex crosslinker (e.g., a pH of 8 or above, more specifically 8.5 to 10.8). Alternatively, a crosslinking inhibitor could be added to preclude crosslinking, even when heated. Sodium bicarbonate, for example, can be a useful crosslinking inhibitor. Also alternatively, latex can be prepared with substantially no crosslinker present (typically NMA), such that a water-dispersible film can form upon drying which can provide strength in the dry state and a reduced degree of strength when moistened, with the possibility of rapid break up when flushed.

Water-soluble, non-colloidal, cationic, thermosetting binders suitable for use with cellulosic fibers are disclosed in U.S. Pat. No. 4,617,124, issued Oct. 14, 1986 to Pall et al., herein incorporated by reference, where epoxide-based versions are said to be preferred, including both polyamido/polyaminoepichlorohydrin resins and polyamine-epichlorohydrin resins, such as Kymene® 557 and the Polycup® series of resins manufactured by Hercules Incorporated (Wilmington, Del.). Related materials can be prepared by reacting epichlorohydrin with condensation products of polyalkylene polyamides and ethylene dichloride. Compositions of this type are disclosed in U.S. Pat. No. 3,855,158 and are exemplified by Santo-res® 31, a product of Monsanto Inc. Another form of this particularly type of binder resin is prepared by the reaction of epichlorohydrin with polydiallyl methyl amine to produce an epoxide functional quaternary ammonium resin. Compositions of this kind are disclosed in U.S. Pat. No. 3,700,623 and are exemplified by Resin R4308, a product of Hercules Incorporated. The disclosures of U.S. Pat. Nos. 3,855,158 and 3,700,623 are incorporated herein by reference.

Water degradable binder fibers can be used such as those used in the coform products of U.S. Pat. No. 5,948,710, issued Sep. 7, 1999 to Pomplun et al., or those disclosed by Jackson et al. in U.S. Pat. No. 5,916,678, issued Jun. 29, 1999, both of which are herein incorporated by reference.

Polycarboxylic acids can also be used as thermally curable binder materials. For example, commonly owned U.S.

patent application Ser. No. 09/426300, "Patterned Application of Polymeric Reactive Compounds to Fibrous Webs," filed Oct. 25, 1999 by Sun and Lindsay, herein incorporated by reference in its entirety, discloses polymeric anionic reactive compounds which can be applied to cellulosic webs to cause crosslinking between the fibers for good strength and bonding. The polymeric reactive compound can be a polymer such as a copolymer, terpolymer, block copolymer, homopolymer, or the like, comprising a monomer with carboxylic acid groups on adjacent atoms (particularly adjacent carbon atoms) that can form cyclic anhydrides in the form of a 5-membered ring, with maleic acid or its derivatives representing specific embodiments of such a monomer. Copolymers of maleic acid or maleic anhydride are thus useful polymeric reactive compounds. Polyacrylic acid can be formed to be useful for the present invention if a significant portion of the polymer comprises monomer that are joined head to head rather than head to tail, to ensure that carboxylic acid groups are present on adjacent carbons. Copolymers of maleic acid or anhydride with acrylic acid or its derivatives are also useful polymeric reactive compounds. A useful commercial compound comprising polycarboxylic acids suitable for bonding fibers in an airlaid web is BELCLENE® DP80 from FMC Corporation, which is a terpolymer of maleic acid, vinyl acetate, and ethyl acetate.

Useful catalysts for curing with polycarboxylic acids include alkali metal salts of phosphorous containing acids such as alkali metal hypophosphites, alkali metal phosphites, alkali metal polyphosphonates, alkali metal phosphates, and alkali metal sulfonates. Useful metal polyphosphonates can include sodium hexametaphosphate and alkali metal hypophosphites such as sodium hypophosphite. When a catalyst is used to promote bond formation, the catalyst is typically present in an amount in the range from about 5 to about 20 weight percent of the polycarboxylic acid. More specifically, the catalyst can be present in an amount of about 10 percent by weight of the polycarboxylic acid. A variety of suitable catalysts are described in U.S. Pat. No. 4,820,307, issued Apr. 11, 1989 to Welch et al., herein incorporated by reference. Other useful catalysts include sodium phosphate, sodium sulfate, imidazole, carbodiimide, triethyl amine, and salts of unsaturated dicarboxylic acids.

Oven-curing of cellulose fabrics with polycarboxylic crosslinkers is disclosed by Kitchens et al. in U.S. Pat. No. 5,042,986, issued Aug. 27, 1991, herein incorporated by reference. Curing is performed at about 150–240 degrees Celsius for 5 seconds to 30 minutes, with the lowest time reported as actually used being 15 seconds. Still faster methods (flash curing) are disclosed in commonly owned, copending U.S. application Ser. No. 09/425810, "Flash Curing of Fibrous Webs Treated with Polymeric Reactive Compounds," filed Oct. 25, 1999 by Sun and Lindsay, herein incorporated by reference.

Binders applied in liquid or solution form to the fibrous web can include any of the binders described in U.S. Pat. No. 5,609,727, issued Mar. 11, 1997 to Hansen et al., herein incorporated by reference.

The binder material can be selected for cost and performance attributes. The binder may optionally contain various fillers, pigments, dyes, etc. if desired.

Binder materials can also be biodegradable and can include polylactic acid and biodegradable polyesters.

Representative Structural Variations

The molded airlaid webs used in the present invention can have non-planar surfaces on both sides of the web, in contrast to many previous attempts at providing contours in absorbent articles by nonuniform distribution of mass, wherein one side of the contoured absorbent layer is typically flat. The three-dimensional structure of the entire web, not just a single surface, in some embodiments can provide flow channels and void spaces on both sides of each molded airlaid web to help guide fluid flow and provide additional absorbent capacity.

The density of the web need not be substantially uniform, and can have density gradients to provide capillary pressure gradients for fluid transport. For example, outer portions of a web can have a higher density, or a lower layer of the web can have a higher density to preferentially wick fluid toward the high density zone. The web can be heterogeneous in composition, such as having a portion of polyolefin fibers in the lower layer and substantially all cellulosic fibers in the upper lay. Such webs can be made by introducing various fibers into the airlaying process at different positions or times during formation of the web, or by joining a plurality of layers to form one integral layer. In some embodiments, the upper layers of a fibrous web can be more hydrophobic than the lower layers to create a dry feel on the skin.

When more than one molded airlaid web layer is used, the topography of each molded airlaid web can be the same or similar to other molded airlaid webs in the core, or one layer can differ from another. For example, large sinusoidal peaks (e.g., base width greater than 4 mm, height about 2 mm or greater, spaced apart in a grid) can be formed in one airlaid web, while the other layer is molded with a sine wave having a different frequency or can have a different pattern altogether to prevent nesting and increase the void volume between adjacent layers. The interaction of the molded areas in two or more of the airlaid webs results in a central hump. The material properties of the layers can give the hump resiliency, such that it can be depressed with a cushiony feel but pops up when released, even when wet, in part by virtue of the bonds in an airlaid web formed from heating or curing of the binder material while the airlaid web is in a three-dimensional state.

The body-side surface of the hump can serve as an intake region. In one embodiment, the hump is at least partially isolated from surrounding portions of the absorbent core by means of a wicking barrier to promote a center fill effect in fluid intake and to prevent fluid from traveling laterally from the hump to the longitudinal sides of the article. Thus, the absorbent core can comprise an outer absorbent member having a central void or depression therein for receiving a central absorbent member comprising the hump formed by multiple layers of molded airlaid webs, with a wicking barrier such as a polymeric film lining the central void to prevent or hinder fluid communication between the central absorbent member and the outer absorbent member. The wicking barrier in this embodiment can provide not only a flow barrier directly between the central absorbent member and the outer absorbent member spanning a vertical distance, but also extends outward from the central absorbent member on the body-side surface of the outer absorbent member to define a ledge or horizontal component of the wicking barrier which can help prevent fluid communication between the central absorbent member and the outer absorbent member when the absorbent core is laterally compressed and bunched together. Principles for product design and construction employing a wicking barrier in the absorbent core are disclosed in commonly owned, copending U.S. patent application Ser. No. 09/165875, "Absorbent Article Having Integral Wicking Barriers," by Chen et al., filed Oct. 2, 1998, herein incorporated by reference.

When a wicking barrier is used in combination with a structure having a central absorbent member and outer absorbent member, the central portion of the absorbent core need not be completely separate from the surrounding outer portions of the absorbent core. Each layer can be a unitary absorbent layer having a contoured central portion which contributes to a hump in the absorbent core, wherein a wicking barrier longitudinally separates the hump from the longitudinal sides of the article without completely isolating the central portion. The use of wicking barriers to separate an outer portion of a unitary absorbent layer from a central portion thereof in the crotch region of the absorbent article is described in more detail in commonly owned copending application "Absorbent Article with Unitary Absorbent Layer for Center Fill Performance," Ser. No. 09/411261 by J. D. Lindsay et al., filed Oct. 1, 1999, herein incorporated by reference. A unitary absorbent layer has an outer portion and an inner portion with a wicking barrier forming part of the boundary therebetween, but the inner and outer portions are still contiguous rather than separate members.

Any known topsheet material can be used in the absorbent articles of the present invention. While the topsheet can be added to the molded airlaid web after molding has been completed, especially good visual definition of the contoured surface can be achieved in some embodiments when the topsheet is disposed over the airlaid web prior to molding. Thus, in one embodiment, a topsheet that can comprise thermoplastic fibers such as polyolefin materials, is disposed over an airlaid web, followed by a molding step to permanently mold the airlaid web to have a three-dimensional topography. The molding step can comprise deforming the airlaid web and topsheet between two opposing molded surfaces (e.g., male and female patterns in cooperative association) as energy is applied to the airlaid web to cause bonding of thermoplastic binder material therein or activation or heat-setting resins. When high temperatures are desired for molding of a cellulosic web, such as above 160° C., above 180° C., above 200° C., or above 230° C., high temperature polymers can be used in the topsheet to prevent undesired melting. Representative high-temperature polymers include polyesters such as polyethylene terephthalate or polypropylene terephthalate, polyamide fibers such as nylon 66 or MII fibers (Material Innovation, Inc., Leonia, N.J.), aramid fibers such as Kevlar™, and the like.

The topsheet can also be apertured, or coapertured with the airlaid web, and may be further provided with slits, such as longitudinal slits along the sides of the airlaid web in the absorbent article.

In another embodiment, the airlaid web comprises elevated "clamshell" structures analogous to the distinctive sectional shapes of the famous Sydney Opera House, wherein raised arcuate projections terminate abruptly with cliff-like precipices ("slotted gaps") that can have open apertures spanning a vertical distance. In this embodiment, an elevated portion of the airlaid web is associated with a slit or other break in the airlaid web to allow the elevated portion to form a vertical gap defined by differing elevations on the respective sides of the slit or break (vertical relative to the plane of the article, assumed to be held in a horizontal position). With the vertical gap facing toward the center of the absorbent article, fluid can be intercepted and trapped that might otherwise run off the article, while the elevated arcuate structures can provide improved body fit and serve as barriers or dams to hinder liquid flow. In forming such "clamshell" structures, the airlaid web can first be slit and then molded to form the elevated portions with vertical gaps opening to void spaces beneath the elevated portions.

Possible uses of the present invention include absorbent articles for intake, distribution, and retention of human body fluids. Examples include feminine care pads and related catamenial devices or sanitary napkins, including "ultrathin" pads and pantiliners and maxipads. Examples of ultra-thin sanitary napkins are disclosed in U.S. Pat. Nos. 4,950,264 and 5,009,653 issued to Osbom; and U.S. Pat. No. 5,649,916, issued Jul. 22, 1997 to DiPalma et al., each of which are herein incorporated by reference in their entireties. Likewise, the present invention can be applied to diapers, disposable training pants, disposable incontinence pants or pull-ups, menstrual pants, other disposable garments such as incontinence pads, bed pads, sweat absorbing pads, shoe pads, bandages, and the like. The present invention can also be incorporated in articles adapted for particular portions of garments to be worn on the human body, gaskets for ostomy bags, and medical absorbents and wound dressings. The articles of the present invention can provide significant leakage protection, fluid center-fill absorptive performance, and other desirable attributes for absorbent articles.

For feminine care pads in particular, the present invention offers surprising advantages in terms of comfort and fit. The combination of two or more layers of molded airlaid webs having overlapping or superposed elevated regions generally yields a sharply defined hump in the absorbent core that appears to have been formed by molding an upper layer around a central pledget or other insert, when in fact no additional material is needed in the absorbent core. Further, the hump has a cushiony, resilient feel, being able to spring back after depression, even when wet, but being more comfortable and compliant than a hump created by insertion of a central pledget beneath an airlaid layer. Further still, the hump has substantial void space beneath it and can have substantial void space between the layers of airlaid web that make up the hump, depending on the topography of each layers and the propensity for the layers to nest together. Non-nesting patterns can be used in some embodiments to increase the void space within or beneath the hump, and to improve the resilience of the hump.

The molded airlaid webs of the present invention can provide useful and novel intake materials for acquisition of large volumes of urine in diapers and related articles while providing improved body fit to prevent leakage. Further, embodiments can also be made adapted to receive runny bowel movement in diapers, holding the fecal matter in void spaces beneath elevated fluid traps accessible through vertical gaps in the topography of the molded airlaid web.

The molded airlaid webs of the present invention are not restricted to structures with a central elevated hump, but can have a somewhat inverted form with a central depression that serves to receive body fluids such as runny bowel movement or urine. The molded web can be placed in an absorbent article with a larger section of absorbent material to interact with other members such as elastic gathers (e.g., elastic gathers disposed in the main absorbent core around the longitudinal edges of the molded web) to form a cup-like shape in use that fits about the crotch region of the user, particularly for male incontinence briefs. In one embodiment for use in male incontinence devices, the molded web has a central molded dome that is concave toward the body rather than the convex toward the body configuration that is often preferred for sanitary napkins. Methods of adapting a rectangular pledget through interaction with elastic gathers to form a cup-like shape in the crotch region are disclosed in U.S. Pat. No. 4,904,249, "Absorbent Undergarment with Fluid Transfer Layer and Elasticized Crotch Design," issued Feb. 27, 1990 to Miller et al., herein incorporated by reference. Replacing the pledget with a molded airlaid web can achieve a useful effect in such articles.

Definitions

As used herein, the term "activate" when used in reference to a binder material in a fibrous web receiving energy from an energy source means to convert the binder material to a state wherein improved bonding of fibers is possible. The binder material can be said to be activated when, for a thermoplastic material, at least part of the binder material becomes viscous upon application of the energy and flows to connect fibers together after it is resolidified,. If the binder is initially a liquid, dispersion, slurry, or other liquid-like material, the binder material is activated when it becomes relatively rigid (e.g., crosslinked or cured) or substantially solid. Thus, both thermosetting resins and thermoplastic materials can be activated by application of heat, though the cellulosic web is not fully set in the case of thermoplastic binder materials until the viscous heated thermoplastic material has resolidified after heat application has ceased.

As used herein, "bulk" and "density," unless otherwise specified, are based on an oven-dry mass of a sample and a thickness measurement made at a load of 0.34 kPa (0.05 psi) with a 7.62-cm (three-inch) diameter circular platen. Thickness measurements of samples are made in a TAPPI-conditioned room (50% relative humidity and 23° C.) after conditioning for at least four hours. Samples should be essentially flat and uniform under the area of the contacting platen. Bulk is expressed as volume per mass of fiber in cc/g and density is the inverse, g/cc.

Other measures relating to the height, elevation, or thickness of the molded airlaid web and its elevated structures are defined hereafter in connection with FIG. 1.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

As used herein, the "crotch region" of an absorbent article refers to that region of the article in closest proximity to the crotch of the user, near the lowermost part of the torso, and resides between the front and rear portions of the article. Typically the crotch region contains the transverse centerline of the article and generally spans approximately 7 to 10 cm in the longitudinal direction.

Many articles of the present invention are intended to be worn near the crotch of a wearer, and thus have crotch regions. However, the present invention can also be applied to other articles such as underarm pads or wound dressings where a crotch region may not exist. In such cases, the article will have a region where fluid intake is intended to occur, termed the "target region." The portion of the article including the longitudinal length of the target region and the full transverse width of the article normal to length of the target region is defined herein as the "target zone." For articles intended to be worn in the crotch, the terms "target zone" and "crotch region" are generally synonymous, hereas "target region" generally excludes the portions of the absorbent core near the ongitudinal sides since the intended area for fluid intake is generally substantially central in the absorbent article.

As used herein, the term "extensible" refers to articles that can increase in at least one of their dimensions in the x-y plane by at least 10% and optionally at least 20%. The x-y plane is a plane generally parallel to the faces of the article. Principles for production of an extensible article are disclosed in U.S. Pat. No. 5,611,790, issued Mar. 18, 1997 to Osborn, herein incorporated by reference. In the case of a sanitary napkin comprising an absorbent core, for example, the article and the absorbent core can be extensible both in length and width. The absorbent article, however, may only be extensible in one of these directions. The article can be extensible at least in the longitudinal direction.

As used herein, the term "flexure-resistant" refers to an element which will support a bending moment, in contrast to an element which will support only axial forces. Likewise, as used herein, "flexure resistance" is a means of expressing the flexibility of a material or article and is measured according to the Circular Bend Procedure described in detail in U.S. Pat. No. 5,624,423, issued Apr. 29, 1997 to Anjur et al., herein incorporated by reference in its entirety. Flexure resistance is actually a measurement of peak bending stiffness modeled after the ASTM D4032-82 Circular Bend Procedure. The Circular Bend Procedure of Anjur et al. is a simultaneous multidirectional deformation of a material in which one face of a specimen becomes concave and the other face becomes convex. The Circular Bend Procedure gives a force value related to flexure-resistance, simultaneously averaging stiffness in all directions. For comfort, the absorbent article can have a flexure-resistance of less than or equal to about 1,500 grams, more specifically about 1000 grams or less, more specifically still about 700 grams or less and most specifically about 600 grams or less. For shaping performance, the central absorbent member as well as the outer absorbent member can have a flexure resistance of at least about 30 grams, more specifically at least about 50 grams, and most specifically at least about 150 grams.

As used herein, the term "flexure zone" refers to a region of an airlaid web that can readily bend due to the shape of the web to permit the web to conform to the body of the wearer. For good body fit along the longitudinal axis, flexure zones extending in the transverse direction are desired. A flexure zone is typically defined by the molded geometry of the molded airlaid web and can be a thin, elongated region of material corresponding to a cusp between two curves regions or to a region where a sudden change in material properties or material curvature occurs. For example, in a longitudinal cross-sectional profile having the shape of two concave down semicircles joined at the ends (similar to the digit "3" rotated to the left by 90 degrees), the middle portion of the material where the two semicircles join has a cusp-like quality. While a cusp in mathematics has no physical dimensions, the cusplike region between adjacent elevated structures can be a region of finite width (distance between the ends of the adjoining semicircles, for example), such as a relatively flat band between domelike elevated regions having a finite length of about 5 mm or less, more specifically about 2 mm or less, more specifically still from about 0.2 mm to about 2 mm, and most specifically from about 0.3 mm to about 1 mm. If the portion of the longitudinal profile shape with a cusplike region extends substantially in the transverse direction (as if the profile shape were extruded into the transverse direction), the airlaid web may fold along the longitudinal axis about a line or band comprising the cusplike region and serving as the flexure zone. The flexure zone can also be a region that has been densified by embossing or thermal or ultrasonic bonding, or that has been weakened by slitting or creased by folding, such that the interaction of the mechanical properties of the surrounding regions with the mechanical properties of the flexure zone promotes bending of the article about the flexure zone in use.

As used herein, the term "horizontal," refers to directions in the plane of the article that are substantially parallel to the body-side surface of the article, or, equivalently, substantially normal to the vertical direction of the article (when the article can be held lying in a horizontal plane), and comprises the transverse direction and the longitudinal direction of the article, as well as intermediate directions. The orientation of components in an article, unless otherwise specified, is determined as the article lies substantially flat on a horizontal surface.

As used herein, the term "hydrophobic" refers to a material having a contact angle of water in air of at least 90 degrees. In contrast, as used herein, the term "hydrophilic" refers to a material having a contact angle of water in air of less than 90 degrees.

As used herein, "Overall Surface Depth" is a topographical measurement of the elevation difference that occurs on the surface of a three-dimensional web. Principles for the measurement and suitable equipment are described by Chen et al. in U.S. Pat. No. 5,990,377, "Dual-Zoned Absorbent Webs," issued Nov. 23, 1999, herein incorporated by reference The measurement is made by examining height data from moiré interferometry for a molded airlaid web resting on a horizontal surface with the body-side surface facing upwards. A profile line that encompasses the extremes of height (maximum and minimum) found on the upper surface (body-side surface) of the molded airlaid web, excluding apertures, is taken and analyzed. The difference in elevation between the 90% material line (a line at an elevation such that 90% of the length of the line along the profile is beneath the surface of the sample) and the 10% material line (a line at an elevation such that 10% of the length of the line along the profile is above the surface of the sample) in the two-dimensional profile comprising the extremes in height is taken as the Overall Surface Depth. For Overall Surface Depths greater than about 1.5 mm, the commercial moire interferometer described in U.S. Pat. No. 5,990,377 may require combination of data from two or more scans made with different focal planes to obtain data over a larger height range than is possible with a single measurement, or a moire interferometer with a larger vertical span can be adapted for use. The Overall Surface Depth can be about 0.5 mm or greater, more specifically about 1 mm or greater, more specifically still about 3 mm or greater, more specifically still about 6 mm or greater, and most specifically about 12 mm or greater, with exemplary ranges of from 4 mm to 10 mm, or from 5 mm to 15 mm, or from 2 mm to 25 mm. The Overall Surface Depth value is related to the simpler Surface Height measurement, hereafter described, but typically the Overall Surface Depth has a somewhat lower numerical value.

As used herein, a "pledget" refers to an absorbent insert within an absorbent core having at least one of a width and a length smaller than the respective width and length of the absorbent core. A pledget is generally used to cause deformation or shaping of an adjoining layer of an absorbent article, and in the present invention, can be of use in shaping a pad or creating a medial hump in the pad for improved fit against the body of the wearer.

The term "sanitary napkin", as used herein, refers to an article which is worn by females adjacent to the pudendal region that is intended to absorb and contain the various exudates which are discharged from the body (e.g., blood, menses, and urine). While the present invention is shown and described in the form of a sanitary napkin, it should be understood that the present invention is also applicable to other feminine hygiene or catamenial pads such as panty liners, or other absorbent articles such as diapers or incontinence pads. The term "feminine care pad" as used herein is synonymous with sanitary napkin.

As used herein, "Surface Height" is difference between the elevation of the highest region of a molded airlaid web as it rests on a flat, horizontal surface (elevation being taken relative to the flat surface) with the body-side surface facing upward and the local thickness of the molded airlaid web at prior to molding. If the web prior to molding did not have a substantially uniform thickness, the local thickness to be subtracted from the maximum elevation is taken at the region where the maximum will occur after molding. Elevation can be measured with any suitable method, including moire interferometry or use of a contact stylus applying a force small enough to not cause any noticeable deformation of the molded airlaid web.

As used herein, the term "transverse" refers to a line, axis, or direction which lies within the plane of the absorbent article and is generally perpendicular to the longitudinal direction. The z-direction is generally orthogonal to both the longitudinal and transverse) centerlines. The term "lateral" refers to substantially in-plane directions having a predominately transverse component. Likewise, "inwardly lateral compression" refers to compression directed from the longitudinal sides of an article toward the longitudinal centerline thereof, applied substantially in the transverse direction.

DETAILED DESCRIPTION OF THE DRAWINGS

Figure 1:
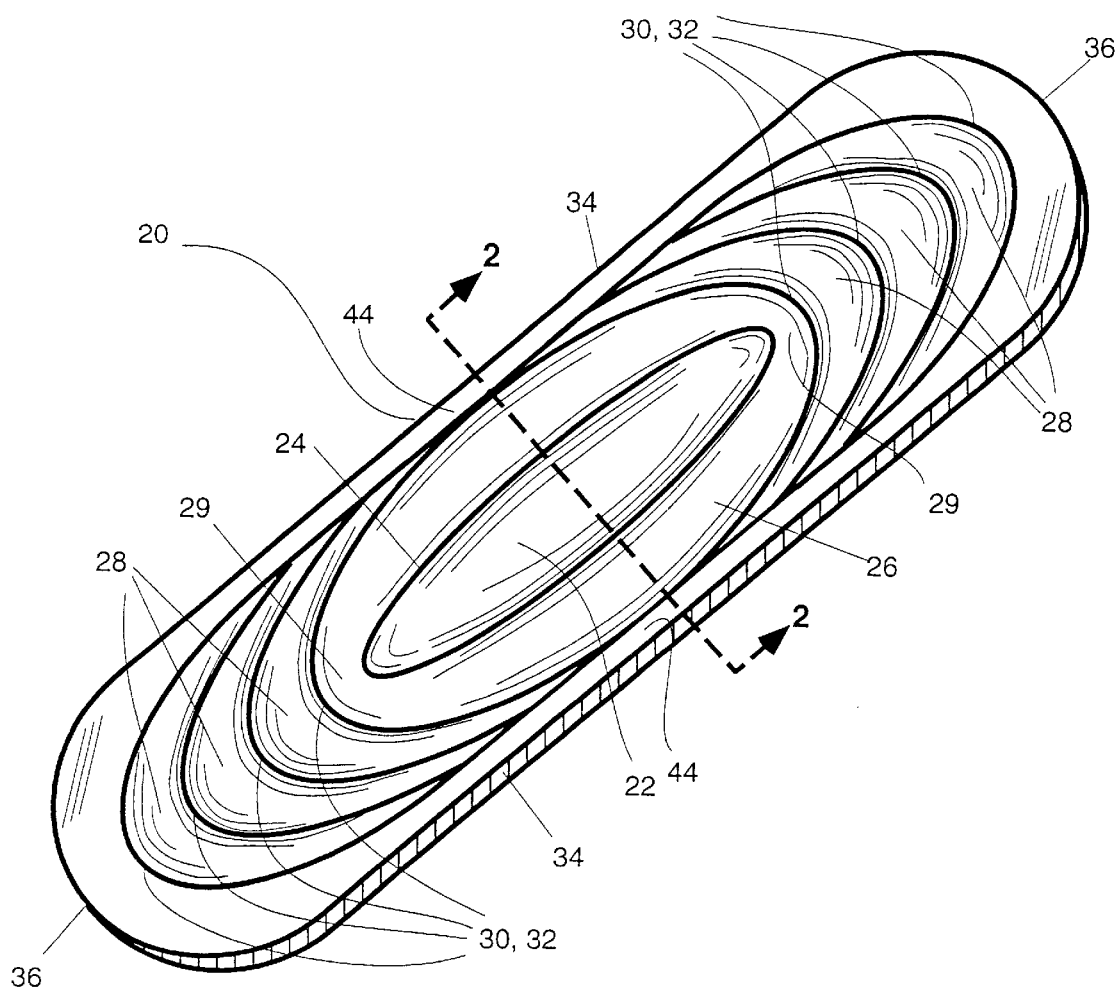
FIG. 1 depicts one version of a molded airlaid web according to the present invention.

FIG. 1 depicts a molded airlaid web 20 according to the present invention, particularly suited for use in a sanitary napkin for feminine care. The molded airlaid web comprises a central longitudinal hump 22 surrounded by a first recessed elongated ring 24, an annular elevated ring 26, and a plurality of elevated regions 28 with recessed regions 30 separating adjacent elevated regions 28, wherein the recessed regions 30 surrounded by elevated regions (such as the elevated regions 28 or the longitudinal ends 29 of the annular elevated ring 26) define transverse flexure zones 32. The web 20 has longitudinal sides 34 and longitudinal ends 36. The edge regions 44 near the longitudinal sides 34 are relatively flat in the embodiment shown, but can also be contoured.

The recessed elongated ring 24 is an example of a transition region between an elevated structure and the surrounding web 20. Transition regions can differ from the flat portions of the web or from the web in the most elevated structures by a material property such as stiffness, density, basis weight, chemical add-on level, degree of thermal bonding, and the like, or can have substantially the same properties as the web in general. Transition regions may be selectively stiffened relative to other portions of the molded airlaid web 20 to increase the resiliency of the central hump 22 or other elevated structures. Stiffening may be achieved by the addition of material, including binder material and crosslinkers, or additional absorbent material, or by densification (e.g., providing a density at least about 30% greater than the web 20 away from the transition region), and the like.

The web 20 may be incorporated in an absorbent article such as a sanitary napkin (not shown), which generally includes a water impermeable backsheet and a liquid-pervious topsheet with an absorbent core sandwiched therebetween. The topsheet may be a nonwoven web, an apertured film, and the like. Hydrophobic material may be deposited directly on the molded airlaid web 20 to provide the benefits of a topsheet. For example, the body-side surface of the molded airlaid web 20 may be treated with hydrophobic matter in discrete zones, as described by Chen et al. in U.S. Pat. No. 5,990,377, issued Nov. 23, 1999, herein incorporated by reference, or may be treated with fluorocarbon materials by any means known in the art, including the plasma treatment method of R. D'Agostino, disclosed in European Pat. Application 0 985 741 A1, published Mar. 15, 2000.

Figure 2:
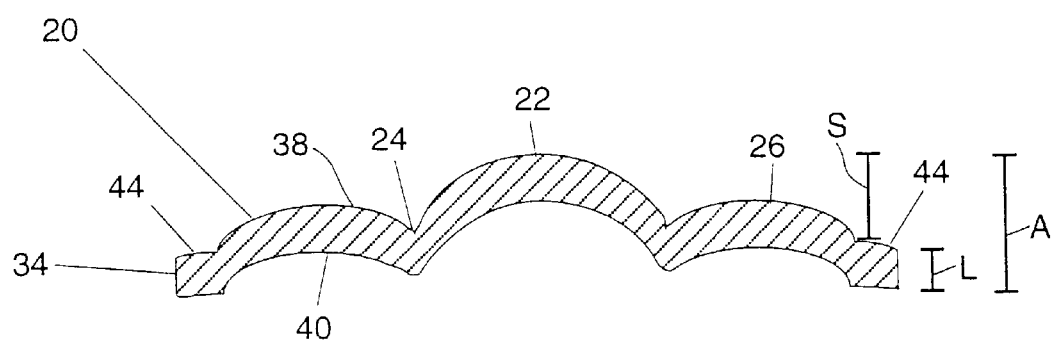
FIG. 2 depicts a transverse cross-section of the web of FIG. 1.

FIG. 2 depicts a transverse cross section of the molded airlaid web 20 of FIG. 1 having a substantially uniform basis weight distribution. The shape of the top surface 38 of the web 20 conforms substantially to the shape of the bottom surface 40 in this embodiment, though the two surfaces need not conform, particularly when the web 20 has a nonuniform basis weight distribution. The web 20 has a typical local thickness L (the thickness of the web 20 itself, here taken as the thickness of the web 20 before molding) and a greater apparent thickness A reflecting the additional height occupied by the molded web 20. The apparent thickness A of the entire web 20 is the height of the highest structure, here the central hump 22, relative to an underlying plane with the molded airlaid web 20 resting flat on the plane and under substantially no compressive load. The apparent thickness A of the web 20 is greater than the local thickness L and greater than the thickness of the edge regions 44. Apparent thickness (or the height of any particular structure) can be measured with an LVDT gauge such as a Mitutoyo thickness gauge (Mitutoyo Digimatic Indicator, Model 543-525-1, Mitutoyo Corp. of America, Aurora, Ill.) controlled to apply zero load as the spindle contacts the surface in measuring the height of the highest structure relative to an underlying flat surface.

The "local thickness" L is the minimum distance from a point on one surface of the web 20 to the opposing surface and generally closely approximates the thickness of the molded airlaid web 20 without regard for the macroscopic shaping imparted by molding. The local thickness of a flat region can be measured as thickness that the region occupies between two parallel platens of 0.5-inch diameter at an applied load of 0.01 psi, which is a load unlikely to cause substantial deformation of typical stabilized airlaid webs.

The "Surface Height" S of the central hump 22 (or of other elevated structures) in a molded airlaid web 20 is also shown.

The ratio A/L can be about 1.5 or greater, more specifically about 2 or greater, more specifically still about 4 or greater, and most specifically from 3 to 7. The Surface Height S can be from about 1 mm to about 25 mm, such as from 5 mm to 15 mm, or from 3 mm to 10 mm.

Figure 3:
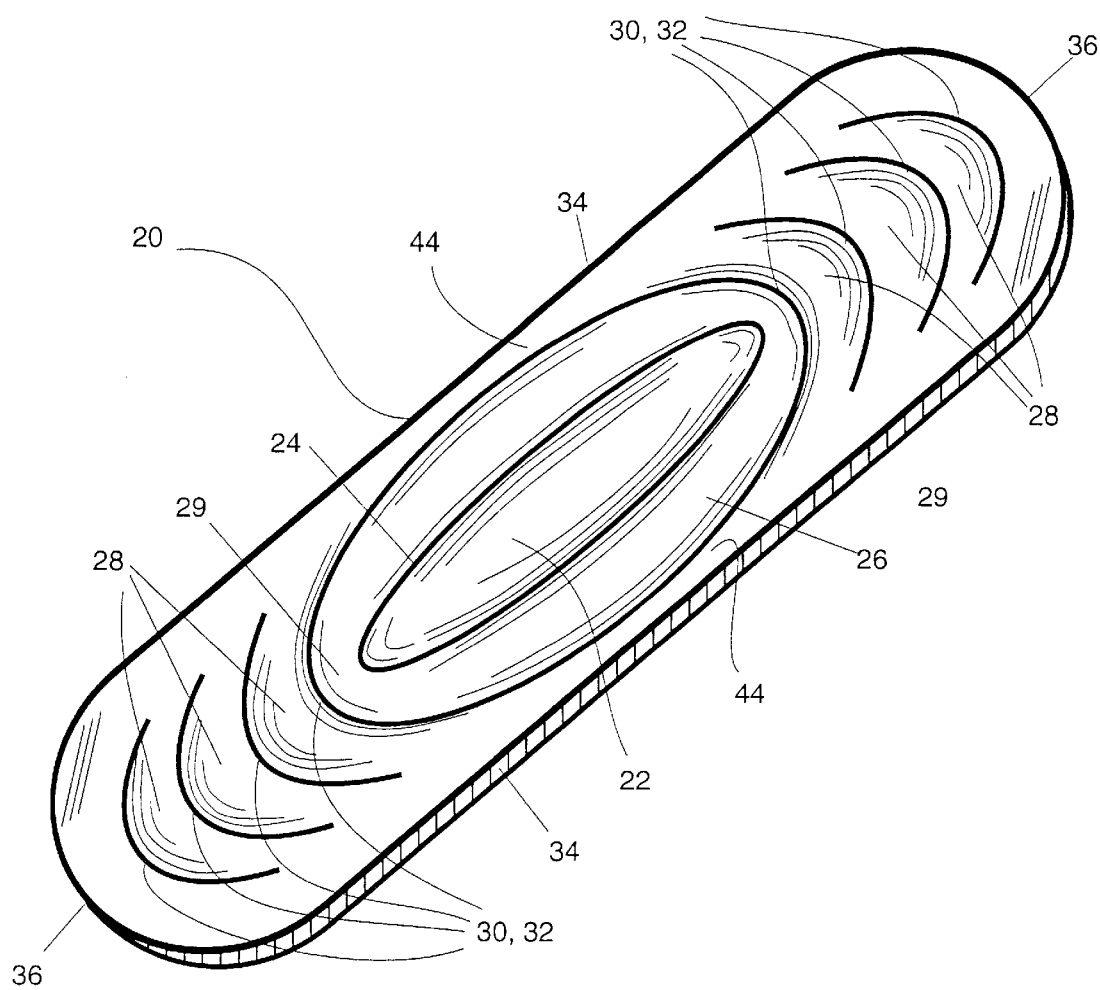
FIG. 3 depicts one version of a molded airlaid web.

FIG. 3 depicts a molded airlaid web 20 similar to that of FIG. 1 except that the recessed regions 30 outside the annular elevated ring 26 do not extend longitudinally to the annular elevated ring 26.

In alternate embodiments, the in-plane curvature of any of the elevated regions 28 can be altered substantially from what is depicted in FIG. 3 and still be within the scope of the present invention. For example, the elevated regions 28, rather than being concave toward the central hump 22 as depicted, could be convex or could be straight transverse lines, or a combination of convex, concave, and straight lines, or more complex shapes such as sinusoidal shapes or the like.

Figure 4:
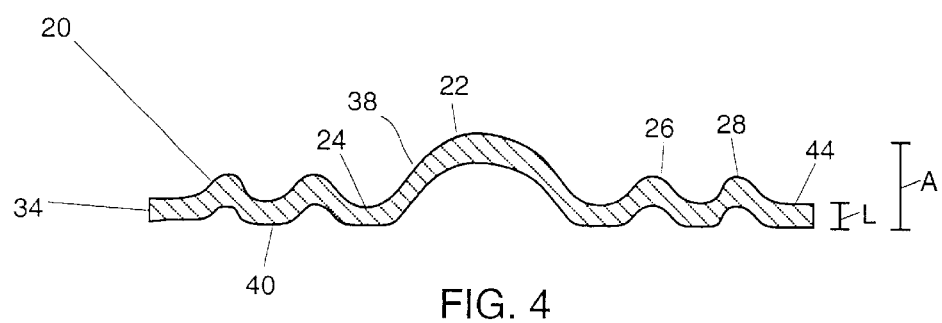
FIG. 4 depicts a cross-section of one version of a molded airlaid web.

FIG. 4 depicts another cross-section of a molded airlaid web 20 with a central longitudinal hump 22 and two smaller elevated regions 26, 28 to either side.

Figure 5:
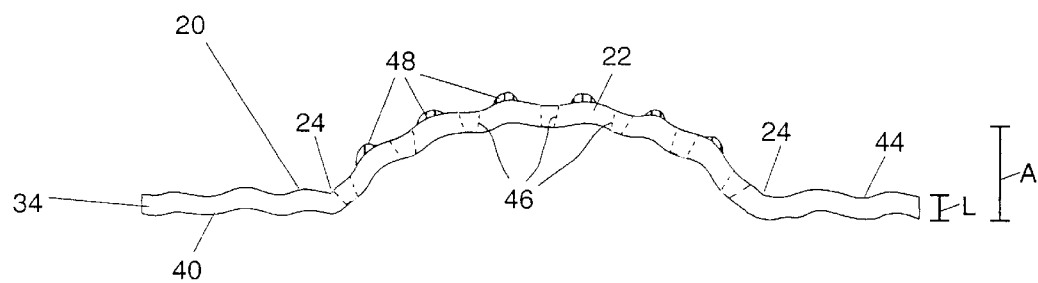
FIG. 5 depicts a cross-section of one version of a molded airlaid web comprising apertures and hydrophobic material.

FIG. 5 depicts another cross-section of a molded airlaid web 20 with a large central longitudinal hump 22 further comprising apertures 46 and deposits of hydrophobic matter 48 on the body-side surface of the longitudinal hump 22 in regions between the apertures 46. The hydrophobic matter 48 promotes a dry, clean feel on the skin, when the molded airlaid web is used in an absorbent article intended to be worn against the body, while the apertures 46 permit rapid entry of fluid beneath the molded airlaid web 20 and into either underlying absorbent material (not shown) or into the void space beneath the longitudinal hump 22.

Figure 6:
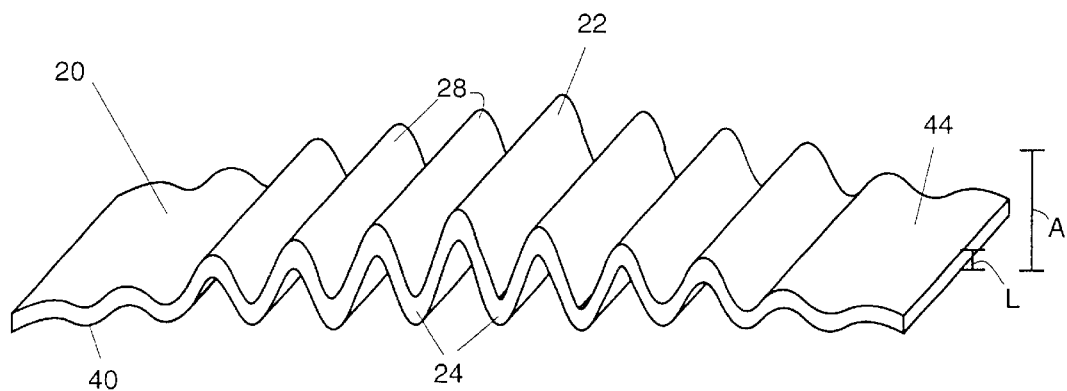
FIG. 6 shows a projection view of -one version of a molded airlaid web.

FIG. 6 depicts a projection view of a molded airlaid web 20 having a shape like a sinusoidal wave whose amplitude tapers away from the center of the web 20, resulting in a central hump 22 of highest amplitude surrounded by other elevated regions 28 and recessed regions 24. Such a web 20 could be one in a stack of multiple molded airlaid webs 20, either apertured or unapertured, for use in an absorbent article such as diaper.

Figure 7:
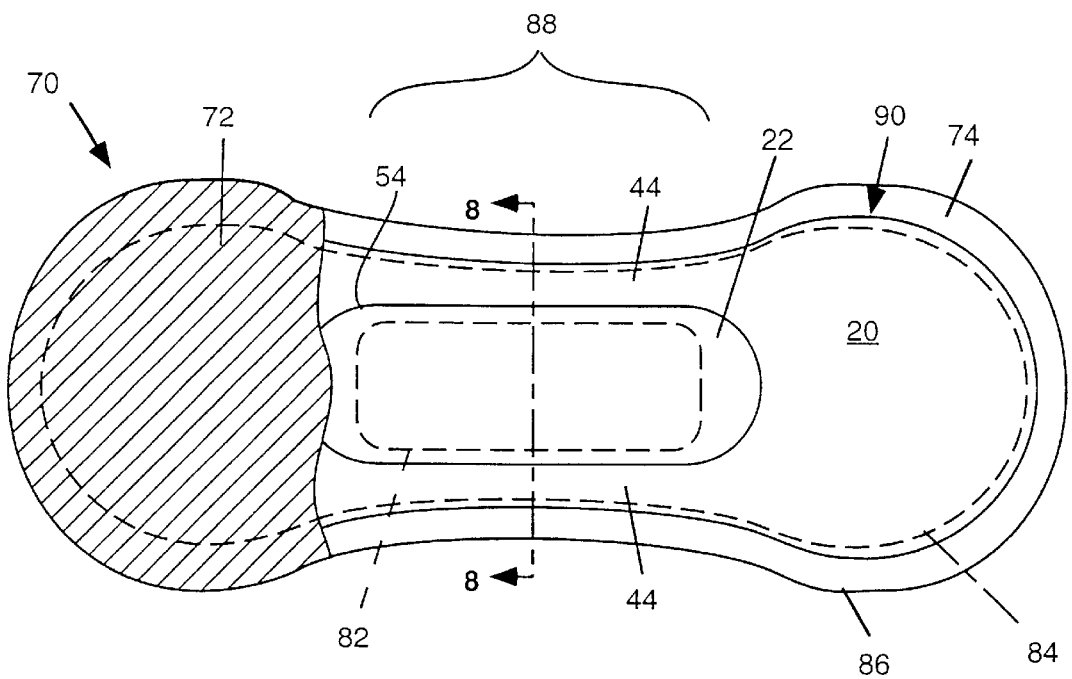
FIG. 7 is a top view of one version of an absorbent article comprising a molded airlaid web.

FIG. 7 depicts the top view of an absorbent article 70 into which any of the molded airlaid webs 20 of the previous Figures can be incorporated, but which specifically depicts the simple structure of the molded airlaid web 20 of FIG. 5 (minus the apertures and hydrophobic matter). The article 70 comprises a liquid pervious topsheet 72, partially cut away to show underlying components, attached to a backsheet 74 at the periphery 86 of the article 70, with an absorbent core 90 disposed therebetween. The core 90 comprises an upper molded airlaid web 20 comprising a central hump 22 and a transition region 54 (which can be a recessed region) between the central hump 22 and the relatively flatter edge regions 44, a central pledget 82 beneath the central hump 22, and a lower absorbent layer 84 beneath the central pledget 82. The central pledget 82 is located within the crotch region 88 of the article 70.

Exemplary topsheets 72 can be made in accordance with U.S. Pat. No. 5,533,991, issued Jul. 9, 1996 to Kirby et al.; U.S. Pat. No. 4,342,314 issued Aug. 3, 1982 to Radel et al. and U.S. Pat. No. 4,463,045 issued Jul. 31, 1984 to Ahr et al. The topsheet 72 may comprise an additional transfer layer to help direct fluid into the absorbent core, as disclosed, for example, in U.S. Pat. No. 4,397,644, issued Aug. 9, 1983 to Matthews et al., herein incorporated by reference, and may be treated with any additive known in the art.

The backsheet 74 is generally impervious to liquids and, thus, prevents menstrual fluid or other body exudates which may be released from the absorbent core 90 from soiling the body or clothing of the uSerial Any backsheet material used in the art for such purposes can be utilized herein. Suitable materials are embossed or nonembossed polyethylene films and laminated tissue, optionally treated with sizing agents and wet strength agents. Breathable films that permit moisture transpiration to occur without significant condensation can also be used. The backsheet 74 may be embossed or provided with odor-controlling materials. The backsheet 74 may also be made of a soft, cloth-like material which is hydrophobic relative to the topsheet 72. An exemplary cloth-like backsheet material is a laminate of a polyester nonwoven material and a film such as is described in U.S. Pat. No. 4,476,180 issued to Wnuk on Oct. 9, 1984. The backsheet can be a polyethylene film having a thickness of from about 0.012 mm to about 0.051 mm. Electrospinning can also be used to create fine denier fibers in an assembly that is breathable but liquid impervious. The backsheet 74 and other components may be biodegradable and/or flushable.

Figure 8:
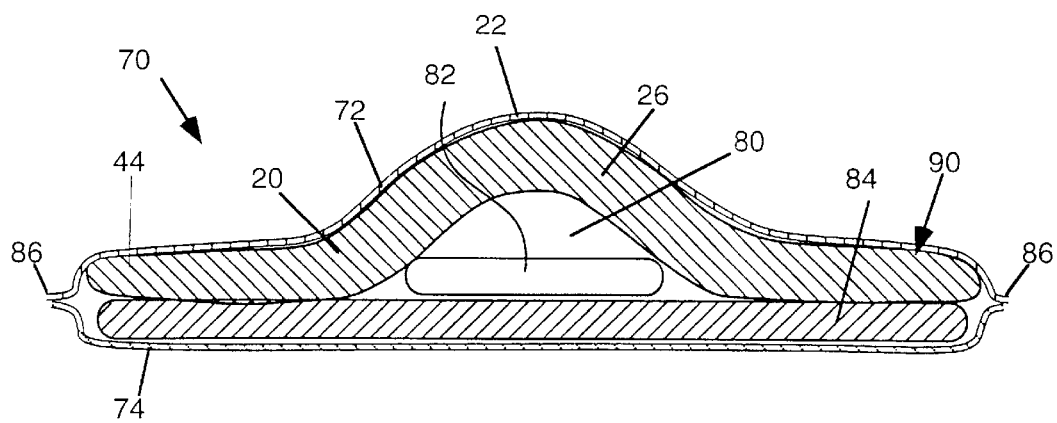
FIG. 8 is a cross-section of the article of FIG. 7.

FIG. 8 provides a cross-sectional view of the article 70 of FIG. 7 taken along the transverse centerline thereof. The central hump 22 of the molded airlaid web 20 provides topography to the body-side surface of the article 70. Beneath the central hump 22 is a void space 80 between the garment-side surface of the molded airlaid web 20 and the backsheet 74. Disposed directly below the void space 80 is the absorbent central pledget 82 which serves to increase the absorbent capacity in the central portion of the article 70 and to provide a level of added resiliency to the central hump 22. Both the molded airlaid web 20 and the central pledget 82 are disposed above a lower absorbent layer 84.

The materials of the absorbent core 90, including the molded airlaid web 20, the central pledget 82, and the lower absorbent layer 84, can each comprise a wide variety of absorbent materials. The central pledget 82 and the lower absorbent layer 84 can each comprise wet laid, air laid, or nonwoven materials, including thermally bonded airlaids (TBAL) made with cellulosic fibers and thermosetting binder material, multiple plies of tissue, comminuted fibers or fluff pulp, coform, laminates of tissue and superabsorbent particles, flexible absorbent foams, peat moss, and the like.

In one embodiment, the absorbent core 90 comprises two or more airlaid webs, such as an upper molded airlaid web 20 and a second lower airlaid web which could be the central pledget 82 or the lower absorbent layer 84, or a plurality of molded airlaid webs. Each web can have a basis weight from about 80 gsm to about 400 gsm.

In addition to one or more molded airlaid webs, the components of the absorbent core 90 can comprise cellulosic airlaid webs of comminuted fibers (commonly termed "airfelt"); cellulose-superabsorbent mixtures or composites; hydroentangled webs comprising cellulosic fibers; composites of synthetic fibers and papermaking fibers such as coform, as disclosed in U.S. Pat. No. 4,879,170, issued Nov. 7, 1989 to Radwanski et al.; rayon; lyocell or other solvent-spun hydrophilic fibers, such as those disclosed in U.S. Pat. No. 5,725,821, issued Mar. 10, 1998 to Gannon et al.; cellulosic foams including regenerated cellulose foams; hydrophilic, flexible foams or absorbent foams produced from high internal phase emulsions (HIPE), such as the foams disclosed in U.S. Pat. No. 5,692,939, issued Dec. 2, 1997 to DesMarais; fiber-foam composites; tissue laminates comprising superabsorbent particles having a gradation in size and/or concentration from one side of the laminate to the other; the foam-structured fibrous absorbent materials of F.-J. Chen et al. disclosed in the commonly owned, U.S. patent application "Fibrous Absorbent Material and Methods of Making the Same," Ser. No. 09/083,873, filed May 22, 1998; absorbent nonwoven webs; cotton; wool or keratin fibers; peat moss and other absorbent vegetable matter, and the like.

In one embodiment, at least one component of the absorbent core 90 comprises a molded, three-dimensional high-bulk wet-laid cellulosic web, such as an uncreped through-air dried web as taught by F.-J. Chen et al. in commonly owned U.S. patent application, Ser. No. 08/912,906, "Wet Resilient Webs and Disposable Articles Made Therewith," filed Aug. 15, 1997 or U.S. Pat. No. 5,399,412, issued to S. J. Sudall and S. A. Engel on Mar. 21, 1995. Such uncreped structures can offer a plurality of flow channels along the surface of the web. The uncreped tissues show excellent wet resiliency and high bulk under load when wet.

Useful sources of cellulosic fibers for the components of the absorbent core 90 include wood fibers, such as bleached kraft softwood or hardwood, high-yield wood fibers, and chemithermomechanical pulp fibers; bagasse; milkweed; wheat straw; kenaf; hemp; pineapple leaf fibers; or peat moss. High-yield fibers such as BCTMP can be flash-dried and compressed into dense pads which expand substantially when wetted. High-yield fiber pads that expand when wetted can be used for the absorbent cores of the present invention, as well as densified regenerated cellulose and curled chemically stiffened cellulose fibers. The fibers in an airlaid web or other component of the absorbent core 90 may be crosslinked. For example, U.S. Pat. No. 5,938,995 issued to Koltisko, Jr. and K. B. Makoui, Aug. 17, 1999, teaches the use of crosslinking agents added to airlaid mats either before or in conjunction with the addition of polymeric binding material to produce resilient airlaid webs.

Figure 9:
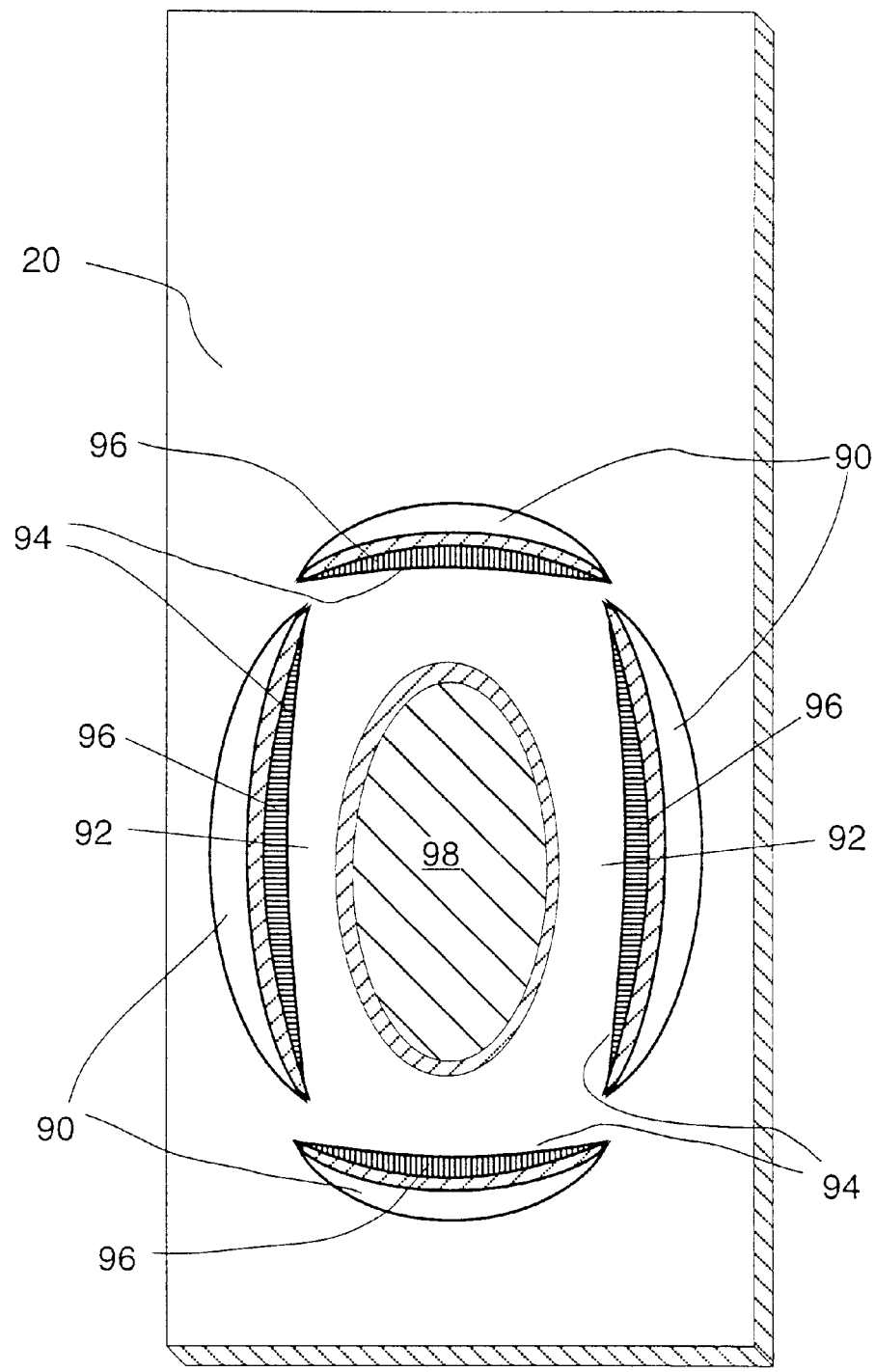
FIG. 9 shows one version of a molded airlaid web with a molded depression and clamshell structures having slotted gaps.

FIG. 9 depicts a molded airlaid web 20 intended for use in a diaper (not shown) to assist in control of runny bowel movement. The molded airlaid web 20 comprises "clamshell" structures 90 that are elevated, molded regions separated from nearby flat regions 92 by slits 94 in the web. During molding, the elevated clamshell structures were molded to create vertical gaps 96 at the slits 94, which can also be termed "slotted gaps" because a vertical slot is formed into which fluid or slurry can enter. The clamshell structures 90 thus can serve as flaps to permit entry of fluid or slurry under the flaps by means of the vertical gaps 96, allowing for interception and containment of fluid away from the body of the wearer of the absorbent article comprising the molded airlaid web 20 of FIG. 9. In other words, the web 20 is molded and slit in a way that provides openings, for the portion of web 20 on one side of the slit 94 has been molded to have a substantially different elevation than the formerly adjacent portion of the web 20 on the other side of the slit 94.

The height of the vertical gaps 96 when the molded airlaid web is unconstrained can be from about 0.3 cm to about 6 cm, more specifically from about 0.5 cm to about 4 cm. The depressed region 98 can have a depth relative to the flat regions 92 of about 0.5 cm to about 3 cm, more specifically from about 0.5 cm to about 1.5 cm, and can further be provided with adjacent clamshell structures.

A molded depressed region 98 can also be provided in the molded airlaid web 20 to further assist in containment of runny bowel movement.

Molded airlaid webs 20 of the present invention can be incorporated in diapers for a variety of purposes. A stack of two or more thin molded airlaid webs 20, such as those of FIG. 4 or FIG. 5, can serve as a surge material for rapid intake of urine, particularly when the molded airlaid web 20 has a low density (e.g., less than 0.1 g/cc), low basis weight (e.g., less than 200 gsm, such as from 60 to 130 gsm), and is apertured. A molded airlaid web 20 with a high-loft central hump can also be used to provide improved contact of the absorbent core of the diaper to the urogenital area.

Figure 10:
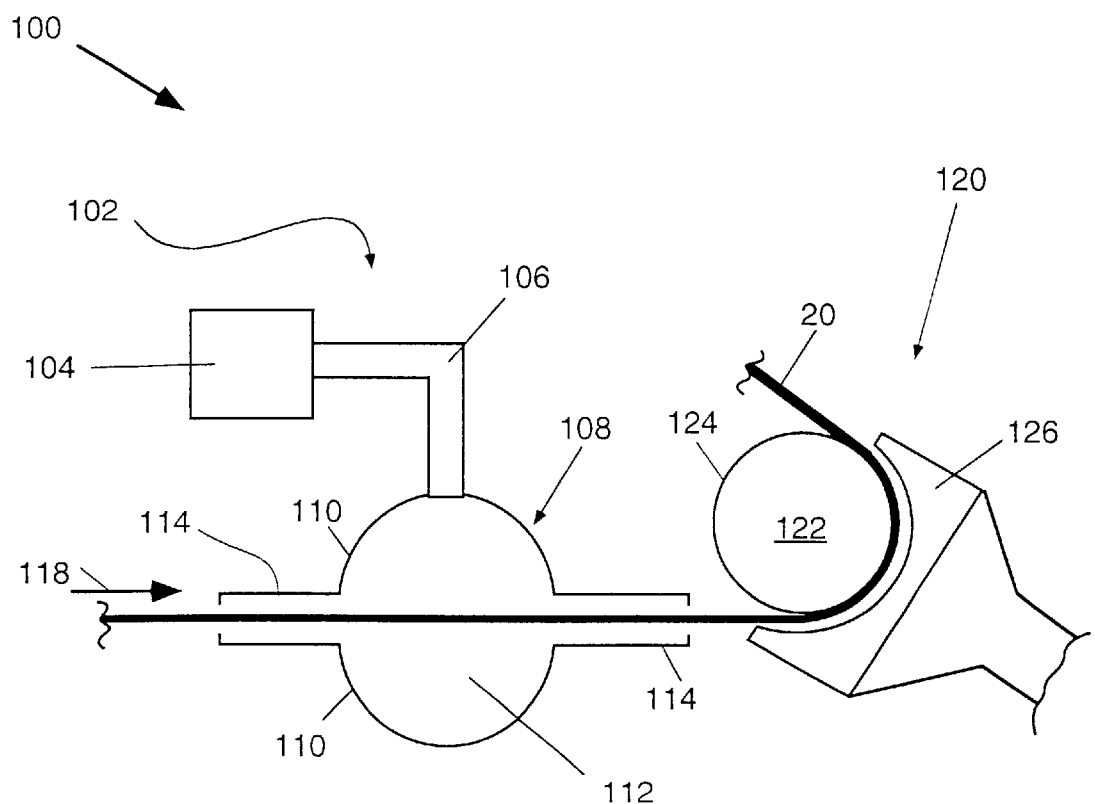
FIG. 10 is a schematic of one version of a molding process of a web comprising a thermoplastic binder material, wherein the web is preheated in a microwave chamber and then molded against a molding roll.

FIG. 10 depicts one version of a molding section 100 of a machine for production of absorbent articles comprising a molded airlaid web 20. The airlaid web 20 travels in the direction indicated by the arrow 118, first entering a microwave preheating unit 102 comprising a microwave generator 104, a waveguide 106, which can be a metallic duct having a rectangular cross-section, and a microwave chamber 108 for applying microwaves to the moving web 20. The waveguide 106 directs microwave energy into the microwave chamber 108 through an aperture (not shown). The chamber can have a geometry that permits microwave resonance in the chamber 108 to efficiently direct energy into the web 20. As depicted, the microwave chamber 108 comprises two semi-cylindrical sections 110 above and below the web to define a cylindrical chamber 108, which can be tunable to achieve good resonance according to the teachings of Lewis et al. in U.S. Pat. No. 6,020,580, issued Feb. 1, 2000, previously incorporated by reference. Leakage of microwave energy from the chamber 108 is reduced by quarter-wave chokes 114 extending outwardly from the chamber 108. The chokes 114 can be made as described by R. C. Metaxas and R. J. Meredith, Industrial Microwave Heating, Peter Peregrinus, LTD, London, 1983, pp. 288–289, and comprise a series of thin bars running in the cross-direction spaced apart at quarter-wavelength intervals on one side of the web, with a polished metal (e.g., aluminum) deadplate on the opposing side of the web. Ferrite is a representative microwave-absorbing material for construction of the bars in the choke 114.

Rolls (not shown) forming a low-pressure nip about the web can also be placed near the chamber to further prevent leakage of microwave energy from the chamber 108.

Principles for the geometry of the waveguide 106 and the aperture into the chamber 108 are given by Metaxas and Meredith, pp. 183–195.

In FIG. 10, the web is depicted as entering the chamber 108 without a carrier belt, but a carrier belt (not shown) could be used. A carrier belt suitably has low susceptibility to microwaves to reduce interference with the heating of the web 20 or the binder material of the web 20.

After preheating, the preheated web 20 enters a molding unit 120 where the web passes over a molding roll 122 which is a suction roll having a three-dimensional porous surface 124 against which the web 20 can be molded by differential air pressure. Hot air may be provided from a heated duct 126 to further assist in molding of the web 20. The molding roll 122 may provide vacuum pressure of about 1 inch of mercury or greater, specifically about 3 inches or greater, more specifically about 8 inches or greater, and most specifically from about 10 to about 20 inches of mercury.

In an alternate embodiment (not shown), the molding roll 122 is replaced with a nip comprising rolls with matched male and female molding patterns that can deform and mold the preheated web 20 while still maintaining, if desired, substantially uniform density in the molded airlaid web 20, at least such that the density of the most elevated structures is substantially the same as the flat regions of the web 20. The surfaces of the rolls in the nip can be heated or unheated.

In this or many other configurations of the present invention, high processing speeds can be obtained. For example, absorbent articles may be processed in a production line with an average machine speed of at least about 0.3 m/s, more specifically about 0.5 m/s, and most specifically about 1 m/s, with an exemplary range of from about 0.6 m/s to about 6 m/s. The subset of high-speed processing methods within the scope of the present invention can offer economic advantages over slower molding methods, such as a method wherein articles are placed by hand in a press and heated by conduction alone for a lengthy period. In general, processing to form a molded airlaid web 20 can occur on automated equipment at industrially relevant processing speeds and production rates, and can occur without the need for significant manual manipulation or handling of the web.

Figure 11:
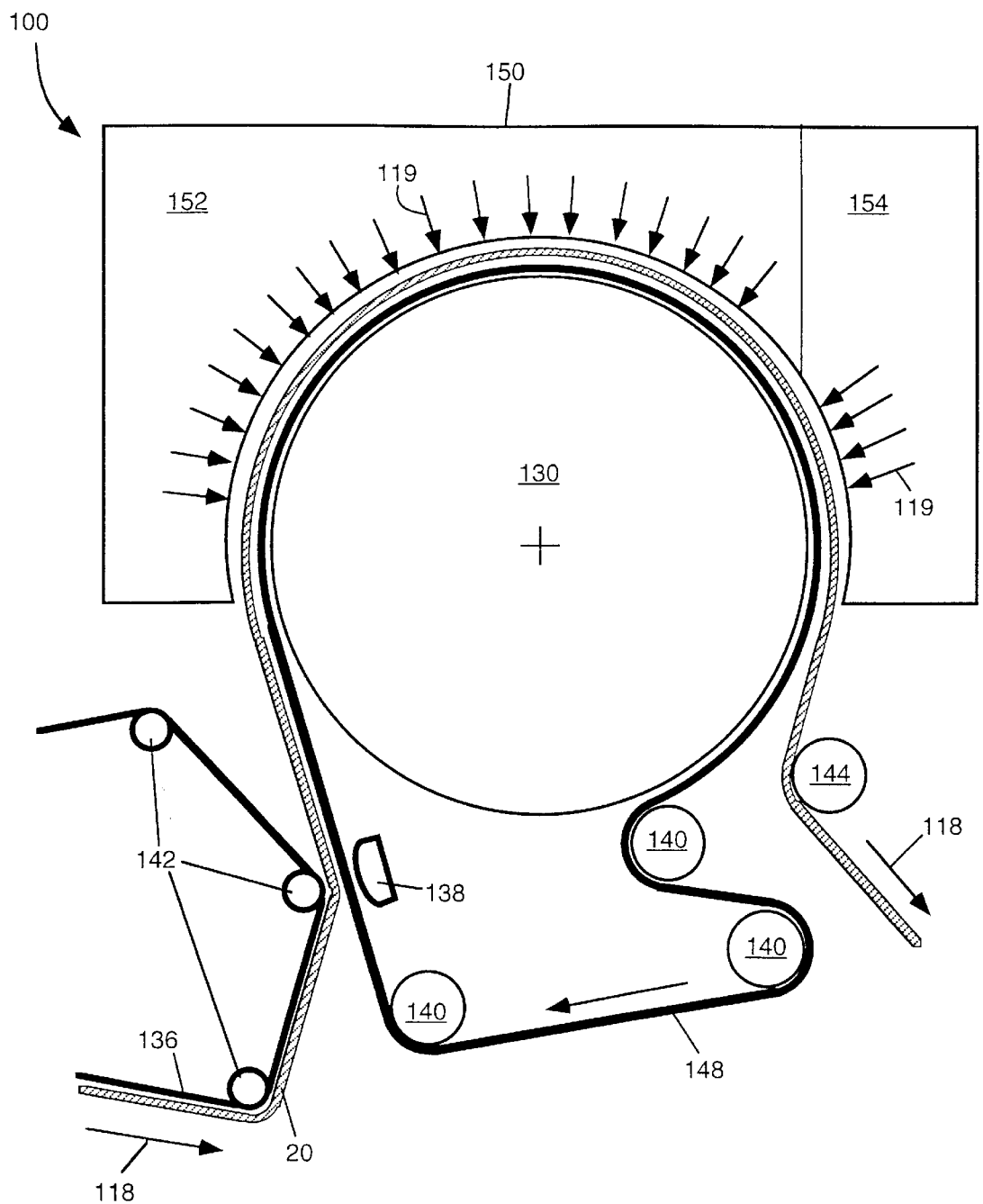
FIG. 11 shows one version of a through-drying system adapted for thermal molding of an airlaid web.

FIG. 11 depicts a differential pressure molding section 100 in which a through-drying roll 130 or other porous roll connected to a vacuum system is used to impart differential air pressure across the web 20 as it rides on a three-dimensional fabric 148 suitable for imparting a desired shape to the web 20. The web 20, traveling as shown by arrows 118, is brought to the molding section 100 by a carrier fabric 136, from which the web 20 is transferred to the three-dimensional fabric 148 (the molding substrate) at a transfer point having a vacuum shoe 138. The web 20 then is carried by the three-dimensional fabric 148 into a hood 150 that has a heated air section 152 and an optional cool air section 154, both of which provide air that flows into the web 20 and into the through-drying roll 130 as shown by arrows 119. Various rolls 140, 142, 144 guide the motion of the fabrics 136, 148.

Heated air supplied by the heated air section 152 of the hood 150 serves to activate the binder material in the web 20 (either causing melting of a previously solid thermoplastic component of the binder material, or causing curing of a liquid binder material) and to enhance the conformability of the cellulosic web 20 under the imparted differential pressure, such that the web 20 conforms to the structure of the three-dimensional fabric 148. The heated web 20 can then be cooled by the optional cold air section 154 of the hood 150 to resolidify any thermoplastic binder material and lock in the shape of the web 20 imparted by the three-dimensional fabric 148. The molded airlaid web 20 can then proceed to further portions of a machine for making absorbent articles, where it may be cut and placed with other components for the final absorbent article.

The three-dimensional fabric 148 may be a woven fabric with significant depth to its topography, such as the sculptured through-drying fabrics of Chiu et al. in U.S. Pat. No. 5,429,686, herein incorporated by reference; the nonwoven molding substrates of Lindsay and Burazin in U.S. Pat. No. 6,080,691, issued Jun. 27, 2000, herein incorporated by reference; or fabrics formed by extrusion of a polymer such as polyurethane on the surface of a woven substrate, such as the SCAPA Spectra™ fabrics (e.g., the fabrics sold under the name of Ribbed Spectra™) of Voith Fabrics, Appleton, Wis., including those disclosed in any of the following: WO 92/17643, published Oct. 15, 1992; U.S. Pat. No. 5,167,771, issued Dec. 1, 1992 to Sayers et al.; or U.S. Pat. No. 4,740,409, issued Apr. 26, 1988 to Lefkowitz; or other three dimensional fabrics suitable for use as a molding substrate in the present invention.

The heated air section 152 of the hood 150 could also provide steam instead of heated air alone for molding of the web. Steam can be used to soften a material and increase its moldability, and is beneficial for certain binder materials that require moisture. For example, steam could soften and/or swell a binding agent such as VINNEX® Dry Emulsion Powder (DEP) binders of Wacker Polymer Systems (Burghausen, Germany), leading to improved bonding with the latex-based binders. In one embodiment, steam treatment equipment is used as disclosed in U.S. Pat. No. 5,968,430, issued Oct. 19, 1999 to M. Naito et al., in which foamed particles are fused together as steam contacts an article. DEP binders can be deposited in an airlaid web during or after production of the web and later activated with moisture prior to or during molding, followed by drying and curing of the binder material. When curing of a latex or other crosslinkable binder material is desired, the web temperature during curing can be about 130° C. or higher, more specifically 150° C. or higher, more specifically still about 160° C. or higher, and most specifically from about 140° C. to about 200° C. In some cases, the degree of crosslinking can be limited for improved flexibility or water dispersibility of the product by restricting the peak temperature of the web. For example, drying and/or curing may be conducted at temperatures not exceeding 180° C., more specifically not exceeding 160° C., more specifically still not exceeding 140° C., and most specifically not exceeding 120° C.

When steam is used, it may be combined with air such that the mixture comprises about 10% or more steam by weight, 20% or more, 50% or more, or 90% or more steam by weight.

In an alternative embodiment, the hood 150 of FIG. 11 is replaced or augmented with one or more hot air knives (not shown), as described in U.S. Pat. No. 5,962,112, issued Oct. 5, 1999 to Haynes et al., previously incorporated by reference.

Figure 12:
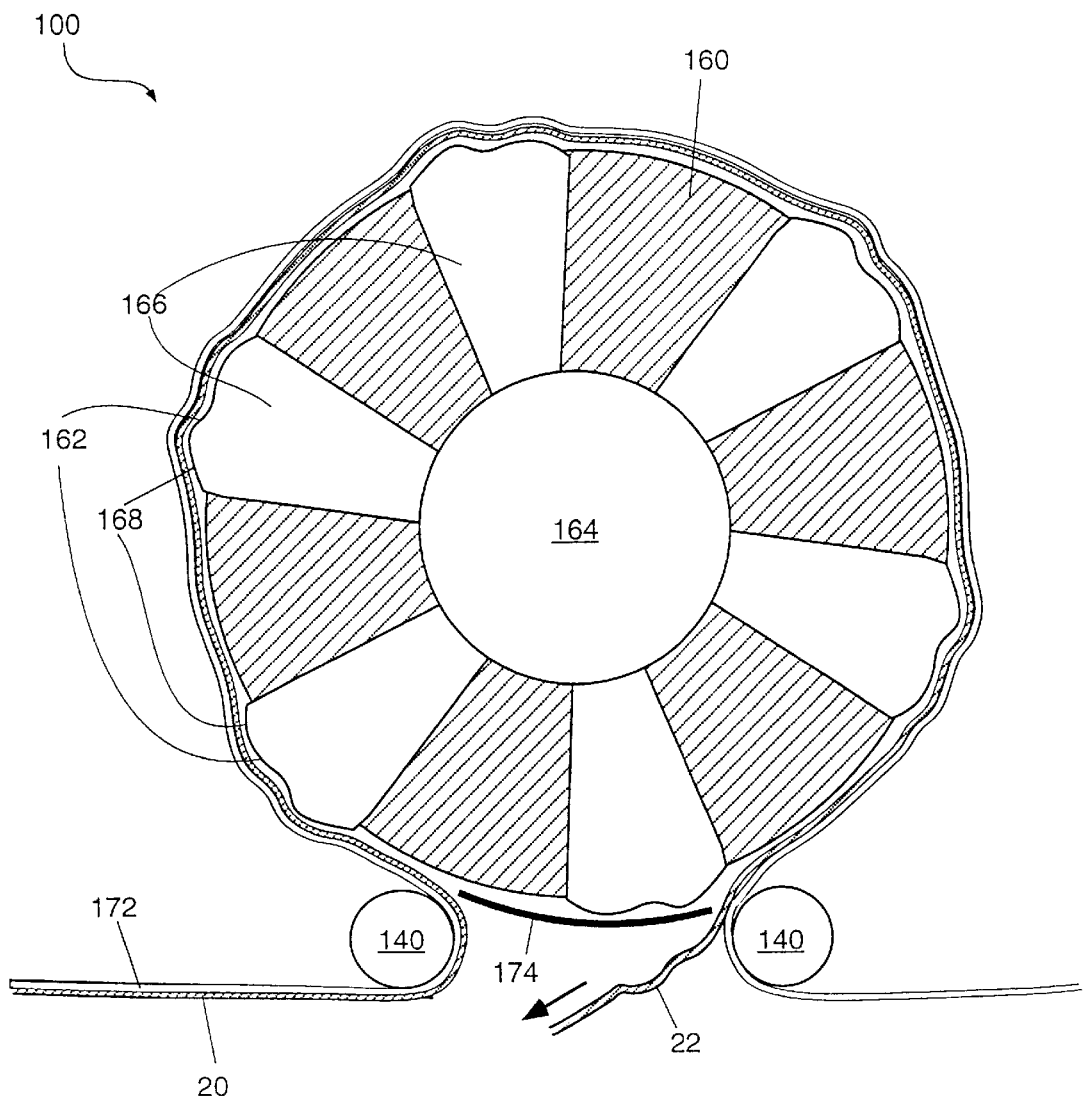
FIG. 12 depicts one version of a rotary molding device wherein energy is applied to the web through an energy-permeable surface of the rotary molding device as the web is held in a three-dimensional configuration.

FIG. 12 depicts a molding section 100 having a rotary molding device 160 which permits application of energy to a web 20 as it is deformed into a three-dimensional shape against a molding substrate 162 on the rotary molding device 160. Energy is applied from a central energy source 164 through a plurality of conduits 166 through an energy permeable surface 168 of the molding substrate 162. The applied energy activates the binder material in the web 20, causing either solid binder material to melt or causing liquid binder material to cure, such that the web 20 can retain the three-dimensional shape imparted to it by the molding substrate 162, even when wetted in subsequent use. (Some cooling of the molded web 20 after leaving the rotary molding device 160 and before any subsequent compressive operations may be necessary when thermoplastic binder material is used for the molded shape to be effectively retained.)

The applied energy can be in the form of microwaves, in which case the conduits 166 can be waveguides and the energy permeable surface 168 of the molding substrate 162 is a microwave-transparent or microwave translucent window made from a suitable material (e.g., Teflon™ or other polymers having low dipole moments). A microwave reflective backing or containment wall (not shown) may be used to surround much of the rotary molding device 160 to prevent leakage of microwave radiation and, in some cases, to help establish resonance of microwave energy focused on the web 20. Microwave absorbing chokes (not shown) may also be installed around the treatment area.

The energy can also be in the form of ultraviolet radiation passing through a UV-transparent (or UV-translucent) window 168. The energy can also be in the form of infrared radiation, general radiofrequency radiation, or even heated air, in which case the energy permeable surface 168 is literally a porous medium such as a wire mesh that permits air to flow into the web 20.

The web 20 is held in place against the rotary molding device 160 with an external belt 172. The belt 172 assists with the molding of the web 20. It can be transparent, opaque, or reflective with respect to the applied energy. For microwave energy, the belt 172 may be substantially free of high dielectric materials to allow microwave energy to pass through the belt 172 and be reflected off a backing (not shown) back toward the web 20, or it may be metallic to reflect microwave energy back toward the conduit 166 or to guide it into the web 20. When heated air flows from the energy source 164, the belt 172 may be permeable to permit hot air to pass through the web 20. The belt 172 can also be impermeable. The tension in the belt 172 can range from about 1000 N/m to 50,000 N/m, and can apply a pressure against the web 20 on the rotary molding device 160 of from about 0.5 kPa to 50 kPa.

A shield 174 in the exposed area of the rotary molding device 160 helps prevent leakage of energy. Further, the rotary molding device 160 can be internally gated to that energy is not applied to a conduit when it is entering the exposed region of the rotary molding device 160, where the web 20 is no longer in contact with the rotary molding device 160.

The molded web 20 as shown can have a variety of complex shapes, including having molded sections featuring a central longitudinal hump 22 and other structures suitable for use in an absorbent article.

Figure 13:
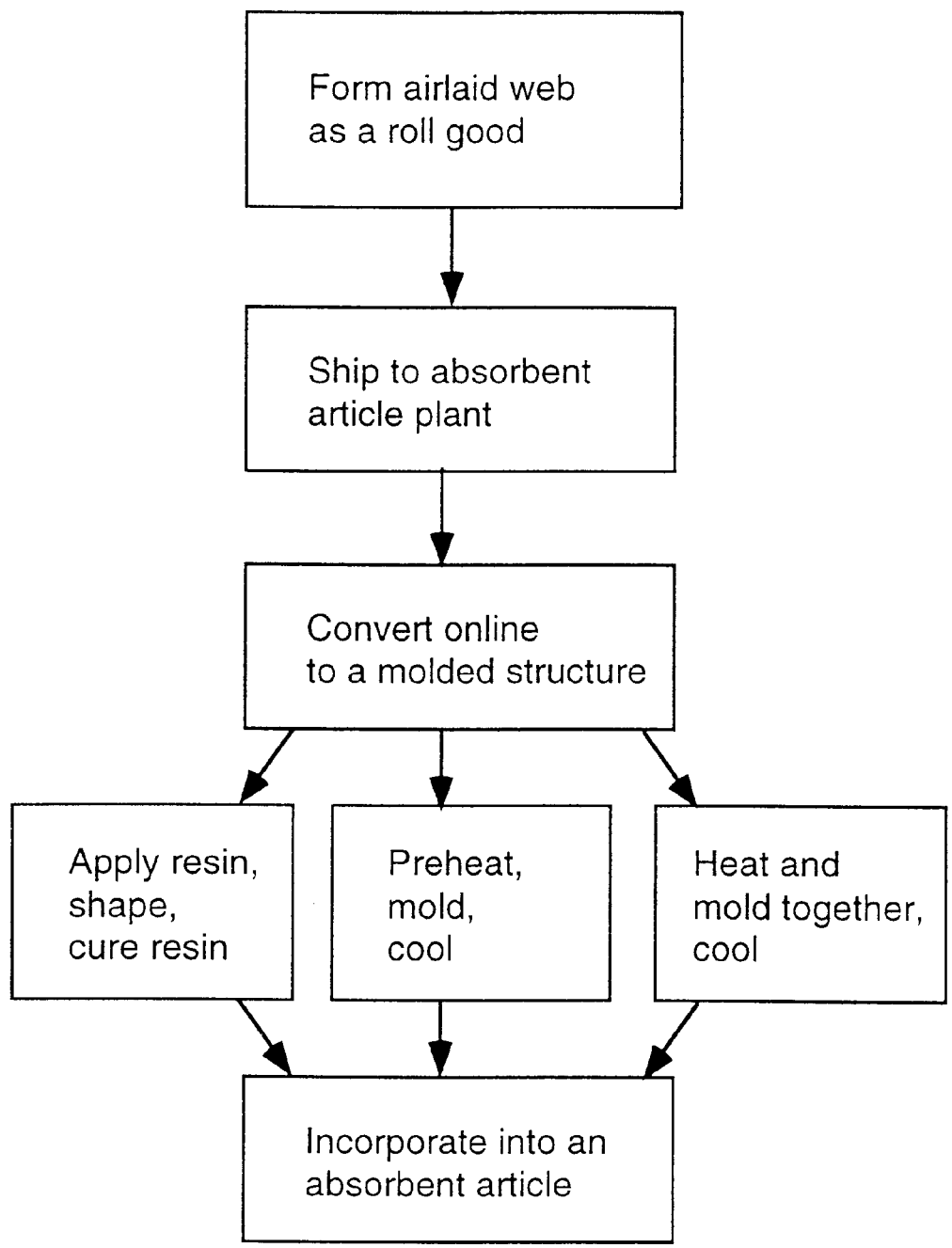
FIG. 13 is a flow chart for one version of a process for making molded airlaid webs from preformed flat airlaid webs, as part of a production process for absorbent articles.

FIG. 13 is a diagram summarizing a basic method for production of absorbent articles comprising molded airlaid webs of the present invention. First, a flat airlaid web is produced using any method known in the art, including the use of Dan Web air former equipment from Dan Web International, Denmark, or according to the method and apparatus of Dunning et al. disclosed in U.S. Pat. No. 3,825,381, issued Jul. 23, 1974, herein incorporated by reference. Airlaid webs may be formed with uniform thickness and basis weight, or may be formed with regions of varying density and basis weight through any method known in the art, including the method of U.S. Pat. No. 6,098,249, issued Aug. 8, 2000 to Toney et al., herein incorporated by reference.

A commercially available air-laid web is AIRTEXT™ 395 air-laid web sold by Fort James Corporation of Green Bay, Wis. AIRTEX™ 395 air-laid web is 100% virgin softwood held together by an acrylic binder. Concert Fabrication Ltee, of Ontario, Canada, also produces a variety of densified airlaid webs held together with thermoplastic binder material. A particularly useful airlaid cellulose-polymer composite material is coform, a hydraulically entangled mixture of pulp fibers and polymer, such as the materials disclosed in U.S. Pat. No. 4,879,170, issued Nov. 7, 1989 to Radwanski et al.; U.S. Pat. No. 4,100,324 to Anderson et al. and U.S. Pat. No. 5,350,624 to Georger et al., the contents of which are incorporated herein by reference in their entireties. The web may be thermally bonded and can be flat with a uniform basis weight, or may have regions of elevated or depressed basis weight.

The airlaid web can be rolled into a roll good for ease of shipment and sent to the production plant where the absorbent articles are made. The production plant (a second production facility relative to the first production facility where the airlaid web was made) can be a separate facility to which the roll good must be shipped for conversion into a molded airlaid web and assembly into an absorbent article. At the production plant for producing absorbent articles, the airlaid web is unwound and processed online, where it is provided with a bulky, three-dimensional structure prior to incorporation into an absorbent article. Adding the high-bulk shape at the plant rather than at the facility where the airlaid web was produced reduces the shipping costs and allows the molded airlaid web to be tailor made according to the specific needs of the product. FIG. 13 depicts three alternatives for the online molding of the web. In the first alternative, the web is treated with a curable resin, then molded, whereupon the resin is cured to lock the fibers in place and provide a molded web. In the second alternative, the web comprises thermoplastic binder material that is preheated, whereupon the web is shaped before the binder material becomes rigid again, and then the web is cooled to lock the structure in place. In the third alternative, the web is simultaneously shaped and heated to cause fusion of the thermoplastic binder material, whereafter cooling of the web locks the structure in place, due to the bonding of the thermally activated binder material. In one embodiment particularly suited for the third alternative, a thermoplastic topsheet is combined with the airlaid web prior to molding such that the topsheet is partially bonded to the airlaid web during heating and becomes thoroughly conformed to the surface of the airlaid web during molding.

Incorporation of the molded airlaid web into an absorbent article can occur by placing one or more layers of molded airlaid webs adjacent to another absorbent component, such as one or more layers of tissue, a flat airfelt or airlaid web, an absorbent foam, and so forth, to form an absorbent core, followed by addition of a topsheet and a backsheet to the absorbent core. The absorbent core may include a layer of liquid-impervious barrier material to separate a central portion of the absorbent core from an outer absorbent member, according to the teachings of Chen et al. in commonly owned U.S. patent application Ser. No. 09/165875, "Absorbent Article Having Integral Wicking Barriers," filed Oct. 2, 1998, previously incorporated by reference. Thus, the molded airlaid web or stack of molded airlaid webs can be cut into a specific shape such as a rectangle or oval comprising a central longitudinal hump, placed over a polymeric wicking barrier (e.g., a polyolefin film), and inserted into a central void space cut in a larger section of absorbent material such as a web of fluff pulp (airfelt) serving as an outer absorbent member, whereby the wicking barrier lines the sides of the molded airlaid web and forms a barrier spanning a vertical distance between the molded airlaid web(s) and the surrounding outer absorbent member. The wicking barrier can also extend horizontally on the surface of the outer absorbent member to further prevent leakage of fluid from the center of the absorbent article toward the longitudinal sides thereof. The composite core can then be adhered to an underlying backsheet and an overlying topsheet.

Combining a plurality of molded airlaid webs can yield an absorbent structure with a plurality of void spaces between each layer, wherein the void spaces are capable of receiving fluid and directing the flow of fluid in preferred directions. The plurality of molded airlaid webs can stack in such a manner that the central portion of the stack has the maximum height, while the stack near the longitudinal sides has a relatively low height.

Figure 14:
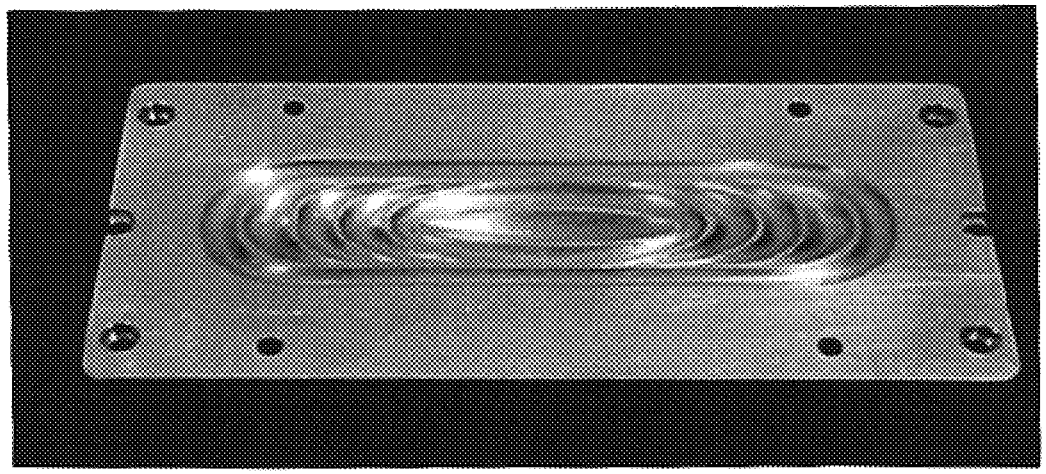
FIG. 14 is a photograph of a metal plate used to mold airlaid webs according to the present invention.

FIG. 14 depicts a contoured aluminum plate used for molding an airlaid web 20 according the present invention. The plate shown is the female version of a matching male-female set. The plates have dimensions of 5 inches by 10 inches in the plane, with a thickness in the uncontoured regions of 0.5 inches. The plate is machined in a pattern of concentric rings, which taper and blend into the surface of the plate moving away from the center of the plates where the features correspond to the central hump of the webs to be molded thereon. The innermost ring defining the central hump has an elliptical shape and the outermost elements resemble rectangles with semi-circular ends. The four intervening shapes gradually change from elliptical to rounded rectangular moving from the inner to the outer. The center and the outermost rings are 0.156 inches above the uncontoured surface of the plate for the male and 0.156 inches below for the female. The successive rings protrude successively less from the outer to the inner. This yields protrusions of, respectively, 0.156", 0.141", 0.125", 0.109", 0.093", and 0.156". The female is the negative of the male.

The plates are heated and an airlaid web placed between the two plates can be molded as conductive heat transfer causes at least partial melting of the thermoplastic binder material in the web.

Figure 15:
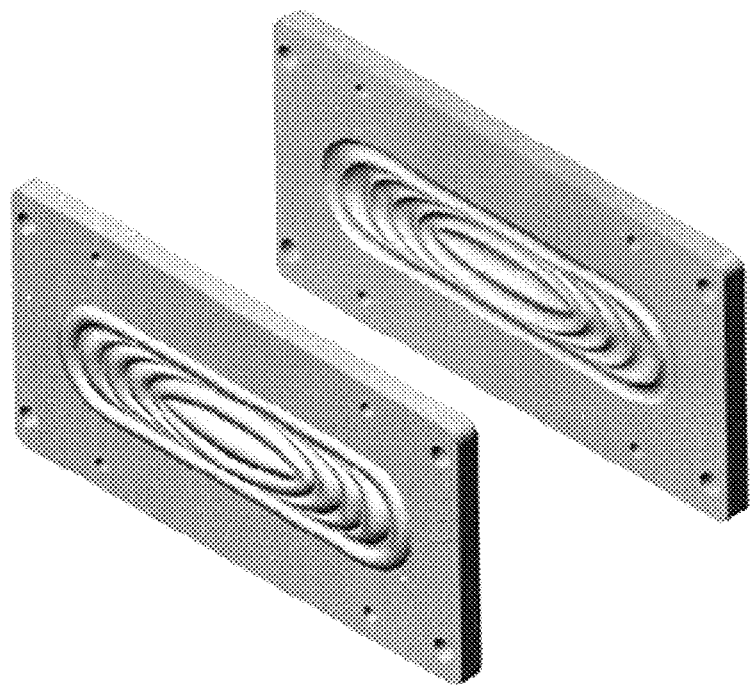
FIG. 15 are computer drawings of matching male and female plates, used to design the plate of FIG. 14.

FIG. 15 is a CAD (Computer Aided Design) drawing of the two matching metal plates referred to above, the machined female version of which is shown in FIG. 14. The drawing was prepared with SolidWorks 99 software from SolidWorks Corp. (Concord, Mass.).

Figure 16:
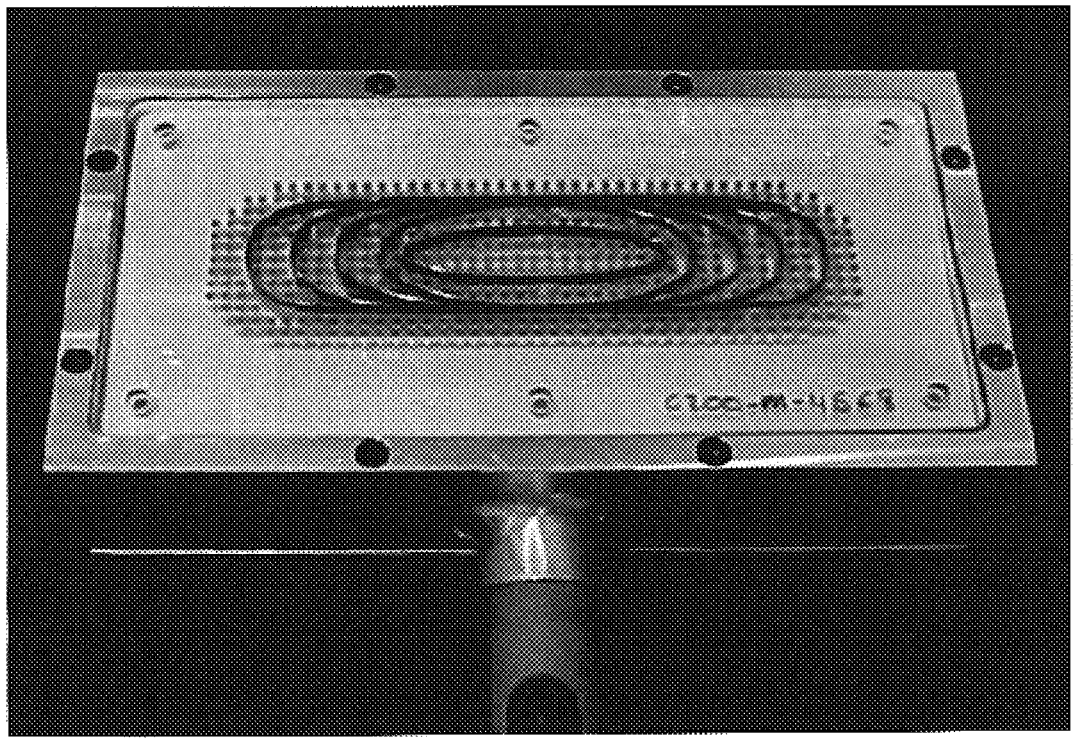
FIG. 16 is a gas-permeable molding system used to mold airlaid webs having designs similar to those of FIG. 1.

FIG. 16 is a photograph of a through-drying apparatus used to mold airlaid webs. A metal plate is provided with multiple holes connected to a vacuum line at the bottom of the photograph. Elevated metal bands rise from the surface of the plate to form concentric rings suitable for molding an airlaid web such as that shown in FIG. 1. The airlaid web is placed over the plate, vacuum is turned on, and heated air from an electric air gun (similar to a blow drier) is applied to the web to soften the binder material and cause effective molding.

Figure 17:
FIG. 17 is a photograph of a section of an airlaid web molded on the molding system of FIG. 16.

FIG. 17 shows a section of airlaid web after molding on the apparatus of FIG. 16.

The web is being squeezed slightly inward from the sides along the transverse centerline, causing the central longitudinal hump to deflect upwards and causing the longitudinal ends of the article to bend upwards as well.

Figure 18:
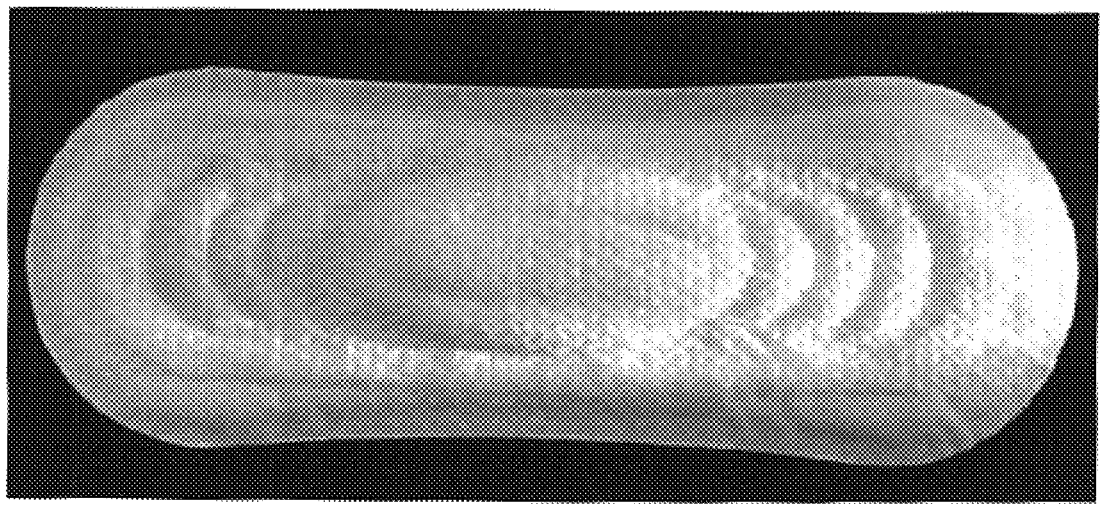
FIG. 18 depicts an absorbent article comprising a molded airlaid web.
Figure 19:
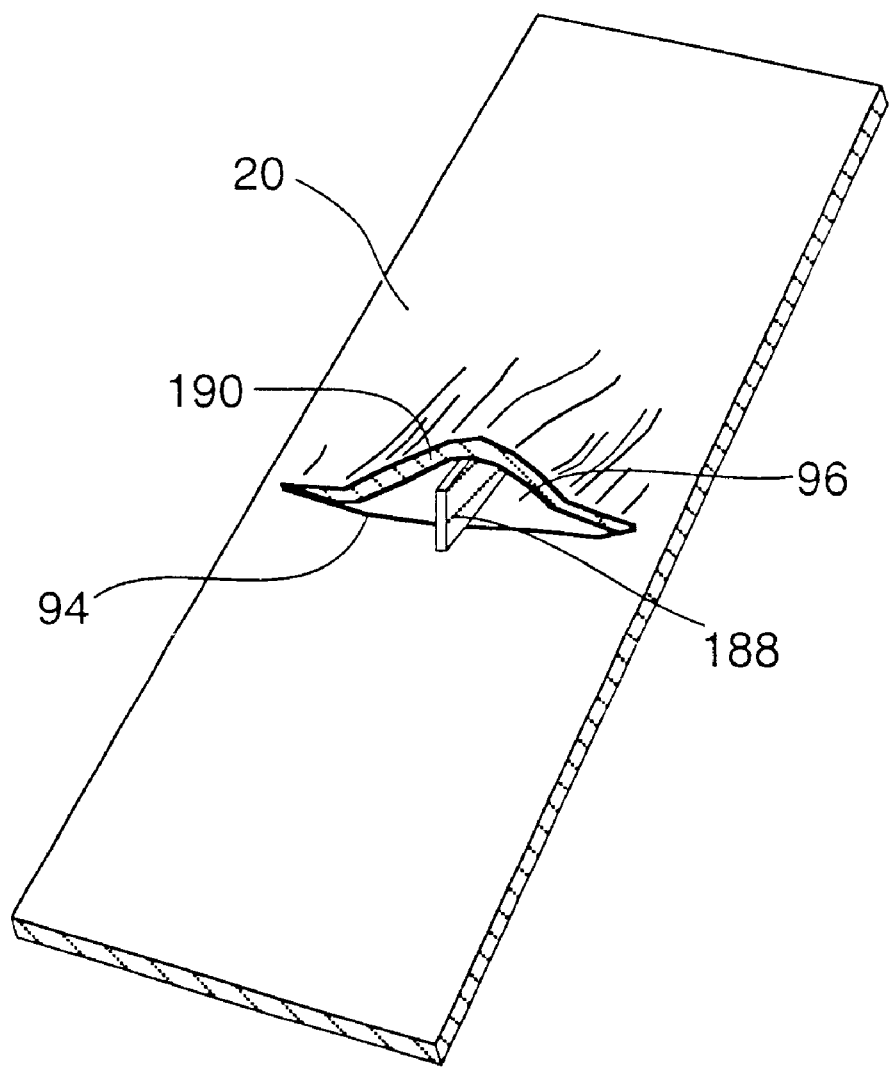
FIG. 19 depicts one version of a simple method for holding open a slot in an airlaid web prior to application of heat to create a slotted vertical gap in the web.

FIGS. 18 and 19 are discussed in more detail hereafter in connection with the Examples.

Other Representative Configurations and Additional Components

The absorbent articles of the present invention can be combined with other functional materials internally (as by adding material into the absorbent material or on the barrier material) or externally (as by joining with additional layers), including but not limited to odor absorbents, activated carbon fibers and particles, baby powder, zeolites, perfumes, fire retardants, superabsorbent particles (including superabsorbent fibers and films as well as free granular material or superabsorbent deposits attached to fibers or other components of the absorbent article), nonwoven materials, plastic films or apertured films, extruded webs, closed cell foams, adhesive strips and tapes, tissue webs, electronic devices such as alarms indicating wetness or leakage and other wetness indicators, opacifiers, fillers, aerogels, sizing agents, antimicrobial agents, enzymes, ion exchange material, or enzyme inhibitors such as urease inhibitors to prevent the production of ammonia.

Skin comfort of an absorbent article can be enhanced with the addition of known skin-care materials such as those disclosed in commonly owned U.S. patent application Ser. No. 09/475825, filed Dec. 30, 1999 by L. Huard et al., herein incorporated by reference; U.S. Pat. No. 4,478,853, issued Oct. 23, 1984 to Chaussee; U.S. Pat. No. 5,871,763, issued Feb. 16, 1999 to Luu et al.; U.S. Pat. No. 3,920,015, issued Nov. 18, 1975 to Wortham, herein incorporated by reference; and U.S. Pat. No. 6,120,783, issued Sep. 19, 2000 to Roe et al.

Elevated structures in the absorbent core or on the molded airlaid web itself may be treated with agents to promote skin health and comfort, including hydrophobic agents to promote skin dryness according to U.S. Pat. No. 5,990,377, issued Nov. 23, 1999 to Chen et al., herein incorporated by reference. The void space beneath elevated structures in the absorbent article may be left vacant or filled with additional absorbent material, such as a pledget of cellulosic fibers, superabsorbent particles, odor-absorbing agents such as zeolites, or combinations thereof.

In some embodiments, for purposes of safety, health, and ease of processing, it is desired that the molded airlaid web be substantially free of crosslinked fibers, or free of fibers that have been crosslinked with materials such as glutaraldehyde, glyoxal, or other formaldehyde-forming materials. The absorbent article or the molded airlaid web thereof can be free of formaldehyde forming susbtances, such as latex containing methylol-based crosslinking agents, CTMP or BCTMP pulp, melamine-based resins, and the like. The absorbent article or the molded airlaid web can also be substantially free of latex or latices, including free of one or more of natural latex or synthetic latex. Natural latex can be a source of allergies, for example, and can be eliminated entirely in some embodiments.

In some embodiments, the absorbent core or the entire article itself is free of urfactants, though surfactants can also be used in other embodiments, such as in bsorbent cores with gradients in surface energy imparted by adding surfactants to one urface of the absorbent core or to a topsheet.

The molded airlaid web can also comprise filler particles and other solids such as alc, calcium carbonate, diatomaceous earth, zinc salts, silica, mica, zeolites, activated carbon, and the like, or can be free of any one or more of the aforementioned solids.

In some embodiments, the absorbent article can be free of rigid materials such as elastic shaping devices, such that the entire article is soft and pliable.

In some embodiments, the molded airlaid web is unembossed (no region has been substantially densified, e.g., the ratio of maximum local density of any portion of the molded airlaid web to the mean local density of the molded airlaid web is less than about 3, more specifically less than about 2 and most specifically less than 1.5).

General Methods for Making the Absorbent Article

Generally, automated equipment can be used similar to the production lines already used for production of sanitary napkins, diapers, and the like, with minor modifications to produce the present invention. Modular systems can be used, wherein the various unit operations in the production line can be moved and replaced with other modules without necessitating a complete rebuild of a machine.

Generally, the airlaid materials used to produce molded airlaid webs will be provided as roll goods, but can be made online in the production facility that produces the absorbent article. The production line can include a hammermill, picker, or other fiberizer known in the art for production of fibers suitable for airlaying processes or formation of a fluff pulp mat, if fluff pulp is to be used. Absorbent material in roll form to be incorporated in the absorbent core can include airlaid webs, coform, mechanically softened pulp sheets, tissue webs, cotton, and the like. Exemplary methods for the production of airlaid webs include those of U.S. Pat. No. 6,000,102, "Apparatus for Air-Laying of Fibrous Material or Granules," issued Dec. 14, 1999 to Lychou.

Likewise, the nonwoven or film components of the absorbent article are also generally provided in roll form. Roll goods are unwound and cut to shape, using methods such as die cutting, slitters, or water jets, and the components placed in proper relationship one to another, typically with online bonding at selected regions provided by spray adhesive, contact with ultrasonic horns or heated embossing elements, or other bonding means known in the art. Components may be moved on continuous belts from one operation to another, and may be further transported with vacuum pick up shoes, jets of air, mechanical pincers, and the like.

Of particular importance is the formation of the molded airlaid web for use as a primary intake layer or for assembly into a multilayered assembly of molded airlaid webs. In one embodiment, an airlaid web comprising thermosetting binder material such as from about 5% to about 20% by weight is provided in roll form, from which a length of airlaid web is continuously withdrawn until the roll is depleted and replaced.

An airlaid web can be formed directly to have a three-dimensional form by using a suitable porous substrate to receive the fibers as they are deposited. Shaped fiber-receiving substrates are typically most useful when spaced apart on a vacuum roll, with a web of highly permeable tissue placed over the roll to help separate the three-dimensionally formed web from the substrate. In this manner, airlaid fibers tend to be deposited with a nonuniform basis weight distribution as well as varying thickness. The loose mat of fibers comprising binder material can then be bonded thermally or by ultrasonic bonding or other means known in the art. Molded airlaid webs produced in this manner have a two-sided topography, in which one side (generally the garment-side surface) tends to be relatively flat and the opposing side (generally the body-side surface) is three-dimensional. Mats formed in this manner lack an attribute that is useful in some embodiments, for the garment-side surface does not have a topography that corresponds to the body-side surface (i.e., the body-side surface is not the inverse of the body-side surface, or, stated differently, the molded airlaid web lacks a stackable shape capable of substantial intermeshing in a stacked arrangement).

Molded airlaid webs with a more stackable geometry can be formed by molded existing airlaid materials provided in roll form. As the length of the unwound airlaid web passes through the apparatus for assembling an absorbent article, it is deposed on a molding substrate, such as a rotating mount, where it is conformed to the shape of the molding substrate as sufficient energy is applied to the web to cause the binder material to partially melt and fuse in contact with cellulosic fibers. Sufficient energy can be applied to the airlaid web prior to the application of significant molding forces that the binder material has softened, such that the airlaid web can be readily molded.

The porous molding substrate can be a shaped wire screen or metal surface finely drilled with holes, and is in pneumatic communication with a vacuum source. The vacuum source can apply sufficient pressure to deform the molded airlaid web against the substrate. Alternatively, applied elevated air pressure remote from the molding substrate can cause the pressure differential needed to conform the web to the substrate. A combination of applied positive pressure on one side and vacuum pressure on the other side of the molded airlaid web can also be effective. As the airlaid web is deformed, heated air is passed through the web for a time period sufficient to cause at least partial melting of the thermosetting binder material. Other energy sources could also be applied, as previously described, but heated air is generally preferred for ease of application and low cost.

Deformation of the web to the molding substrate can also be achieved with the application of mechanical pressure rather than pneumatic pressure or in addition to pneumatic pressure, though is pneumatic pressure has the advantage of maintaining a substantially uniform density in the web after it is molded. When a web is pressed between two opposing surfaces to apply mechanical pressure, the web can be substantially uniformly compressed. Heated air may still pass through the web if both surfaces are porous, but ultrasonic energy or thermal energy applied by conduction may also be applied, with conduction being a less preferred vehicle for delivery heat because of the z direction temperature gradient that will be imposed which may result in excessive thermal bonding near the heated surface or surfaces. If conduction is used, the web can wrap a heated roll or contact heated plates or other heated surfaces.

After heat has been applied to partially melt the binder material, a burst of cooler air can be passed through the web to help set the binder material before the airlaid web is removed from contact with the molding substrate. The airlaid web may be cut to shape before, after or during molding. The web is then joined to other elements, including the backsheet, the topsheet, and a lower absorbent layer or other molded airlaid webs, if desired, to form the absorbent article.

If desired, the web can be apertured, embossed, foreshortened, pleated, corrugated, needlepunched, perf-embossed, calendered, mechanically softened, brushed, creased, or treated with chemical additives such as surfactants before, after, or during thermal molding, though many mechanical web treatments are suitably carried out on the intact web prior to cutting of the web into discrete sections for incorporation into absorbent articles. Useful embossing designs include sine wave patterns in the longitudinal direction, series of dots forming recognizable patterns such as circles or flowers, and the flared central lines depicted in commonly owned pending application Ser. No. 09/165,875, "Absorbent Article with Center Fill Performance," filed Oct. 2, 1998 (see especially. FIG. 22A therein), herein incorporated by reference. Slits, folds, creases, embossments, and the like can also be applied in the patterns shown in commonly owned pending application Ser. No. 09/165,871, "Absorbent Article Having Good Body Fit Under Dynamic Conditions," also filed Oct. 2, 1998, herein incorporated by reference.

The topsheet and backsheet can be joined to the airlaid web after molding has been completed, but it has been discovered that greatly improved visual definition of the molded airlaid web's topography can be obtain in the absorbent article if the topsheet is attached to the airlaid web, suitably with adhesives, prior to or during molding, such that the topsheet intimately follows the surface topography of the molded airlaid web. Care should be taken that the topsheet does not lose its usefulness by melting during the molding step.

In one embodiment, a cellulosic lower absorbent layer such as fluff pulp is provided with a central void by stamping or cutting, the void being sized to receive a central pledget and a molded airlaid web or multilayered assembly of molded airlaid webs disposed over the pledget. An optional wicking barrier may be placed over the longitudinal side walls of the central void or depression prior to insertion of the molded airlaid web or multilayered assembly of molded airlaid webs to provide barrier functionality for the central portion of the absorbent article. The article is then provided with a topsheet and a backsheet, along with other optional elements.

In addition to previously cited patents, useful methods for construction of absorbent articles and assembly of various components are further described in U.S. Pat. No. 4,578,133, "Method and Apparatus for Applying Discrete Strips to a Web of Material," issued to Oshefsky et al., Mar. 25, 1986; U.S. Pat. No. 5,560,793, "Apparatus and Method for Stretching an Elastomeric Material in a Cross Machine Direction," issued to Ruscher et al., Oct. 1, 1996; U.S. Pat. No. 5,591,298, "Machine for Ultrasonic Bonding," issued to Goodman et al., Jan. 7, 1997; and U.S. Pat. No. 5,656,111, "Method for Construction of Mechanical Fastening Tapes," issued to Dilnik et al., Aug. 12, 1997.

EXAMPLES

Several examples of absorbent articles were made with the materials listed in Table 1 below:

TABLE 1

Basic materials used in construction of absorbent articles for the Examples.

| Component | Manufacturer | Description |
| --- | --- | --- |
| Topsheet | | |
| Spunbond material | Kimberly-Clark Corp. | 0.6 osy polypropylene spunbond web with 0.3% add-on of surfactant (described below), pin apertured |
| Surfactant treatment | ICI Americas, Inc. | ethoxylated castor oil with sorbitan monooleate |

TABLE 1-continued

Basic materials used in construction of absorbent articles for the Examples.

| Component | Manufacturer | Description |
|---|---|---|
| Adhesive | National Starch and Chemical Co. | NS-34 series: slot-coated, pinstripe pattern, applied at a level of about 5 gsm or less. |
| Fluff | Alliance Forest Products | Coosa River CR54 debonded softwood pulp comminuted with a hammermill |
| Airlaid-superabsorbent web | | |
| Completed web | Concert Fabrication, Ltee | 50% softwood fibers, 45% superabsorbent particles, 5% binder fibers with a basis weight of 500 gsm and a density of about 0.1 g/cc. |
| Fibers | Weyerhaeuser Co. | 0% NB-416 bleached southern softwood kraft, 50% crosslinked southern softwood kraft |
| Binder fibers | KoSA, Inc. (Salisbury, NC) | Celbond #255: PET core, activated co-polyethylene sheath, 50/50 core/sheath ratio, concentric, 2.8 dpf, with T-255 fiber finish |
| Superabsorbent particles | Stockhausen | Granular superabsorbent particles |
| Densified airlaid webs | | |
| Completed web | Concert Fabrication, Ltee | 90% softwood fibers and 10% binder fibers with overall densities of 0.08–0.2 g/cc. |
| Fibers | Weyerhaeuser Co. | NB-416: bleached southern softwood kraft |
| Binder fibers | KoSA, Inc. (Salisbury, NC) | Celbond #255: PET core, activated co-polyethylene sheath, 50/50 core/sheath ratio, concentric, 2.8 dpf, with T-255 fiber finish |
| Coform | Kimberly-Clark Corp. | 60% bleached kraft southern softwood, 40% polyethylene, basis weight of 135 gsm |
| Impervious wicking barrier | | |
| Polyolefin film, white | Edison Plastics Co. | A low density polyethylene, 18 gsm, about 1 mil in thickness |
| Backsheet | | |
| Polyolefin film | Edison Plastics Co. | A low density polyethylene, 20 gsm, 2 mil gauge after being embossed with a fine square pattern, coated with contact adhesive on one side |
| Adhesive | National Starch and Chemical Co. | NS-34 series, less than 15 gsm added, slot-coated, pinstripe pattern |
| Garment adhesive | National Starch and Chemical Co. | NS-34 series, less than 45 gsm applied, slot coated, two 15 mm side lines |
| Release paper | Akrosil Inc. | White base sheet, one side coated with silicone release agent, other side printed |

Example 1

Through-air Molding

A 175 gsm airlaid densified web (as described in Table 1) served as the lower layer of the absorbent core. The 175 gsm airlaid lower absorbent member was cut to a dumbbell shape with a length of about 21.5 cm and a width at the transverse centerline of 5 about 6 cm. The dumbbell-shaped lower absorbent member was placed on the backsheet (as described in Table 1) comprising a polymer film provided with contact adhesive. Above the lower layer was placed a molded rectangular rounded central strip of a densified airlaid web having dimensions of 18.7 cm by 3.7 cm. The densified airlaid strip was as described in Table 1, with a density of about 0.1 g/cc and a basis weight of about 175 gsm. Molding was done with vacuum pressure pulling the sheet against the apparatus of FIG. 16 while heated air was applied to the web from a Variable Temperature Heat Gun, No. 8977, Milwaukee Electric Tool Corp., Brookfield, Wis. Vacuum was applied with a NILFISK GMPC 115 Shop Vac (Nilfisk-Advance, Malvern, Pa.) connected to a metal vacuum box 6 inches wide×11 inches long×3 inches high. The unmolded airlaid material, prior to being die cut, was placed on top of the molding form, as described in connection with FIG. 16. The sides away from the molded region were restrained with weights (total mass of about 7 pounds) on either side of the molding surface to prevent transverse contraction of the airlaid web. The vacuum source was turned on. As air flowed through the web, the Variable Temperature Heat Gun was used to apply heated air to the web. The gun was moved steadily to provide uniform heating until the web visibly increased in conformance to the molding surface. When the airlaid is visually deemed to have been formed into the desired shape, the heat source was removed and continued passage of air through the web was permitted, drawn by the vacuum source, to cool the web and solidify the binder fibers.

The spunbond topsheet as described in Table 1 was then placed over the entire article, with edges extending well beyond the lower absorbent member. Adhesive held the cover in place on the molded airlaid web. The laminated structure was then cut with a dumbbell-shaped die having dimensions greater than the lower absorbent member (24.4 cm long, 8 cm wide at the transverse centerline) to provide a rim of backsheet material and cover material around the lower absorbent member in an absorbent article having good integrity provided in part by the contact adhesive on the polymeric film. After cutting, the pad had the general appearance shown in FIG. 18.

Example 2

An absorbent article was made similar to that of Example 1, except that two molded airlaid webs were used to form the absorbent core. The upper layer had a basis weight of 225 gsm and a density 0.12 g/cc, while the lower layer had a basis weight of 175 gsm and the same density, 0.12 g/cc. Both webs were initially molded with the heated-air device of FIG. 16, as described in Example 1. The surface height of the molded airlaid webs was approximately 6.5 mm and the web thickness was about 1.5 mm. After molding, the upper layer was cut to a racetrack shape (rectangle with semi-circular ends) 202 mm long and 54 mm wide. The lower layer was cut to an hourglass shape 226 mm long with end lobes having a maximum width of 74 mm and a narrow center with a width of 64 mm. The upper layer was centered over the lower layer with a transfer delay layer placed between the two airlaid layers. The transfer delay layer was a pink spunbond web with a basis weight of 0.8 ounces per square yard, fibers of 2.2 denier, and treated with 0.3% add-on of surfactant, as listed in Table 1. The transfer delay layer was cut to a width of 70 mm and a length of 226 mm. The transfer delay layer was centered below the upper layer and the excess width of the transfer delay layer was used to wrap the sides of the upper absorbent layer. Two-sided tape strips, about 3 mm wide and 226 mm long, were used to attach the wrapped transfer delay layer to the upper surface of upper layer. The tape strips were placed between the folded-over portion of the transfer delay layer and the upper surface of the upper layer.

A longitudinal strip of tissue 177 mm by 35 mm was centered beneath the lower layer, and the assembly was placed on a backsheet layer and below an apertured spunbond cover sheet (0.6 ounces per square yard, with a 54 mm wide central region that had been pin apertured), with the adhesive material of the backsheet joining the cover sheet around the periphery of the article. The assembly was centered in an hourglass-shaped die having a length of 238 mm, and a maximum width at the end lobes of 86 mm, with a minimum width at the center (transverse centerline in the crotch region) of 76 mm. The resulting absorbent article had the general appearance of the article of FIG. 18. It is believed that the transfer delay layer can serve as a wicking barrier to help prevent leakage from the sides of the article. It is also believed that the tissue layer enhances body fit by preventing adhesive bonding between the central portion of the lower layer and the backsheet, such that the lower layer can flex away from the backsheet and toward the body when laterally compressed from the sides by the legs of a uSerial

Example 3

An article was made according to Example 2 except that a pledget cut from a layer of airfelt was inserted between the upper absorbent layer and the transfer delay layer. The airfelt layer (comminuted bleached softwood kraft fibers deposited by air after hammermilling to form an unbonded fluff layer) had a basis weight of 340 gsm and a density, after calendering, of 0.17 g/cc.

Example 4

An article was made according to Example 2 except that the lower absorbent layer was made from airfelt rather than a molded airlaid web. The airfelt web was a 400 gsm softwood layer embossed with a sine wave pattern and further joined to a tissue layer on the upper surface. Two straight embossed lines in the crotch region were also provided, each about 70 mm long and 2 mm wide, spaced about 40 mm apart, embossed with the tissue in place.

Example 5

An article was made according to Example 3 except that the lower absorbent layer was replaced with an outer absorbent layer made from a ring of airfelt, and the transfer delay layer was replaced with a white polymeric film having adhesive on both sides, such that the film lined the central void of the outer absorbent member to serve as a wicking barrier. The outer absorbent layer was made from airfelt made from the 340-gsm fluff of the pledget in Example 3 (basis weight 340 gsm). It was cut to an annular hourglass shape having an outer hourglass shape 226 mm long, with lobe widths of 74 mm and a central width of 64 mm, with a rounded rectangular hole 188 mm long and 44 mm wide. The white film (the impervious wicking barrier of Table 1, provided with adhesive on both sides) was wider and longer than the final article, so upon final cutting of the article, it would have the same dimensions as the article. The film was placed over the airfelt ring. A strip of tissue, 177 mm long by 35 mm wide, was placed over the wide film, centered with respect to the central void in the airfelt ring. The pledget, having a basis weight of 650 gsm and a density of 0.14 g/cc, was then placed over the tissue, centered with respect to the central void in the airfelt ring, and the upper absorbent layer (a molded airlaid web) was centered above the pledget. The composite core was then sandwiched between a backsheet and a topsheet and cut to the same dimensions as the article of Example 2.

Example 6

Thermal Molding with Matched Plates

The molded metal plates described above in connection with FIG. 14 were used for thermal molding of a 175-gsm densified airlaid web comprising thermoplastic binder fibers, as described in Table 1. The plates were mounted in a facing relationship to opposing press surfaces of a heated press (Model 8-14.5, Boston Electric Heating, Milwaukee, Wis.), with the female plate on the lower surface and the male plate on the upper surface. The press surfaces were provided with drilled holes for tightly mounting the molding plates with screws to the lower and upper press surfaces.

The heater was set to a temperature of 190° F. and given sufficient time to heat the molding plates (at least 30 minutes). The airlaid strip, a section of 175 gsm airlaid according to Table 1, was placed over the lower (female) molding surface. The stroke for the heated press was set to 4 seconds. The start button was pushed, bringing the platens together with the airlaid in between. When the stroke was complete and the platens returned to their initial positions again, the molded airlaid web was carefully removed from the plates and allowed to cool to solidify the binder fibers.

A well-defined molded airlaid web was created in this manner, apparently having a substantially uniform density.

Molded airlaid webs made in this manner were cut and placed in absorbent articles according to Examples 2 and 3.

Example 7

Slotted Gaps

FIG. 19 depicts a molded airlaid web 20 provided with a slotted gap 96. A sheet of the densified airlaid web 20 of Table 1 was selected having a density of 0.14 g/cc and a basis weight of 250 gsm. It was cut into a strip 5.5 cm wide and 23 long. A transverse slit 94 having a length of 4 cm was cut at the longitudinal center of the strip 20 (normal to the longitudinal axis), the slit 94 having ends equidistant from the longitudinal sides of the strip 20. A glass microscope slide 188 turned on its side and wedged into the slit, as shown in FIG. 19. The slide had a width of 2.3 cm (and a length of 7.3 cm), giving the arch 190 in the airlaid web a height of about 2.3 cm.

The arched region 190 of the airlaid web 20 was then heated with a 1400 W heated air gun (Variable Temperature Heat Gun, No. 8977, Milwaukee Electric Tool Corp., Brookfield, Wis.) with a heating setting of about 75% of maximum, with air applied from a distance of 15 cm over a 30 second period with gentle oscillation of the gun to distribute the applied hot air over the arch, including the central 30% of the surface area of the airlaid strip 20. The assembly was allowed to cool for 60 seconds at room temperature (23° C., 50% relative humidity). The arch 190 maintained its stability and even after being compressed down to the same plane as the rest of the strip 20, was able to rebound to a height of about 1.5 cm. Such an arch 190 is suitable for receiving runny feces, or other body fluids or multiphasic materials (slurries, etc.).

Example 8

Microwave Trial

A 2450 MHz microwave unit from Richardson Electronics (LaFox, Ill.) with a 6 kW generator was constructed using a rectangular waveguide (approximately 4 cm by 9 cm cross-section) to bring the microwaves to a split cylindrical resonance chamber having a 10 cm diameter and quarter-wave chokes, constructed according to the principles of U.S. Pat. No. 6,020,580, issued Feb. 1, 2000 to Lewis et al., previously incorporated by reference (see also FIG. 10). A reel was provided of 4-inch wide airlaid web with a basis weight of 175 gsm and thermoplastic binder fiber, according to Table 1. The airlaid web was unwound and passed through the chamber and attached to a mechanically driven winding roll with variable speed drive to pull the web through the resonance chamber. Once the web began to move through the resonance chamber, the power was turned on for the microwave generator to heat the web. Web speeds varied from about 150 feet per minute to 800 feet per minute, and power levels ranged from 1.5 kW to 6.7 kW. The microwave energy rapidly heated the web, achieving a web temperature above 105° C. at 600 feet per minute web speed (105° C. surface temperature was measured two feet downstream from the chamber, after some cooling had occurred). Higher power would be required at this speed investigated to heat the web to higher temperatures, such as 150° C. or 175° C.

Though no carrier belt was used in this example, microwave-transparent belts could be used in related embodiments to support the web or to carry cut sections of fibrous webs into a resonance chamber.

Example 9

A bleached southern softwood kraft airlaid web bonded with 5% latex was prepared with a basis weight of about 150 gsm and a thickness of 2.3 mm. One piece of the dry, flat web was sprayed with an aqueous solution comprising 2% BELCLENE® DP80 (polymeric anionic reactive compound, FMC Corp.) and 1% sodium hypophosphite catalyst at a wet add-on level of 150% (1.5 g of solution per g of fiber). The web was dried at 105° C. and then cured for 3 minutes at 175° C. Another piece was left untreated. The untreated airlaid web and the cured, treated web were both saturated with water and pressed by a load of 0.9 pounds per square inch for 15 minutes, then each air dried. The treated airlaid web retained 67% of its original thickness, while the untreated web retained only 29% of its original thickness, showing that the polymeric anionic reactive compound was successful in providing wet resiliency and preserving the bulk of the web.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of preparing an absorbent article with an industrial production machine, comprising:
    a) providing an absorbent web comprising cellulosic fibers and solid binder material;
    b) moving the article through the production machine at an average machine speed of at least 0.3 meters per second;
    c) heating the binder material with an energy source as the web moves to elevate the temperature of the binder material such that it becomes viscous;
    d) deforming the web against a molding surface while the binder material is still viscous to impart a three-dimensional shape having an overall surface depth of at least 2 mm;
    e) reducing the heating of the absorbent web to allow the binder material to cool;
    f) disposing the absorbent web between a backsheet and a topsheet; and
    g) attaching a portion of the topsheet to a portion of the backsheet.

2. The method of claim 1, wherein heating the binder material comprises application of radiofrequency energy.

3. The method of claim 2, wherein the radiofrequency energy comprises microwaves, and wherein the binder material is microwave sensitive.

4. The method of claim 3, wherein heating the binder material further comprises passing the web through a tunable microwave resonance chamber.

5. The method of claim 4, wherein the tunable microwave resonance chamber has a substantially cylindrical cross-section.

6. The method of claim 1, wherein heating the binder material comprises application of heat by conduction from the molding surface.

7. The method of claim 1, wherein heating the binder material comprises directing a flow of heated fluid toward the web.

8. The method of claim 7, wherein the heated fluid travels with an oscillatory component in its velocity.

9. The method of claim 7, wherein the molding surface is gas permeable and wherein a heated gas passes through the web.

10. The method of claim 7, wherein the heated fluid comprises at least 20% by weight of steam.

11. The method of claim 7, wherein the heated fluid comprises at least 90% by weight of heated air.

12. The method of claim 9, wherein the molding surface comprises a porous member selected from a three-dimensional through-drying fabric, a three-dimensional wire mesh, and a three-dimensional rigid surface provided with fine holes.

13. The method of claim 1, wherein heating the web and deforming the web occur simultaneously.

14. The method of claim 1, wherein heating the web occurs prior to deforming the web.

15. The method of claim 1, wherein heating the web occurs after deforming the web.

16. The method of claim 1, wherein disposing the topsheet above the absorbent web occurs prior to deforming the web against a molding surface.

17. The method of claim 1, wherein the absorbent web prior to treatment is substantially flat.

18. The method of claim 1, wherein the binder material has a dielectric loss constant substantially greater than that of cellulose.

19. The method of claim 1, wherein the binder material comprises a bicomponent fiber.

20. The method of claim 1, wherein the maximum temperature of the web does not exceed 160° C. during heating of the binder.

21. A method for forming an absorbent article comprising:
  a) providing a wound roll of a flat airlaid web of cellulosic fibers at a first production site, wherein the airlaid web also comprises at least 5% thermoplastic binder material;
  b) unwinding the roll at a second production site to supply the airlaid web to a molding section of a production system for producing absorbent articles;
  c) heating the airlaid web within the molding section;
  d) deforming the heated airlaid web against a molding substrate within the molding section to create a molded airlaid web having a three-dimensional shape with a surface height of least 5 mm; and
  e) attaching the molded airlaid web to liquid-impervious backsheet.

22. The method of claim 21, wherein the molded airlaid web comprises a central longitudinal hump and a plurality of transverse flexure zones imparted by molding.

23. The method of claim 21, wherein heating the web comprises application of microwave energy to the web.

24. The method of claim 21, wherein heating the web comprises application of heated air that passes through the web.

25. The method of claim 21, wherein heating the web and deforming the web occur simultaneously.

26. The method of claim 21, wherein heating the web occurs prior to deforming the web.

27. The method of claim 21, wherein heating the web occurs after deforming the web.

28. A method of preparing an absorbent article comprising:
  a) providing a first and second airlaid webs, each comprising cellulosic fibers and binding material, the webs each having two longitudinal sides;
  b) deforming each web against a molding surface to having a three-dimensional shape, the shape being relatively flat near the longitudinal sides of the section and more highly contoured near the center of the section;
  c) heating each web sufficiently, while deformed against a molding surface, to cause the binder material to become bonded to the cellulosic fibers;
  d) disposing the first web above the second section web to form a stack of molded airlaid webs;
  e) disposing the stack of molded airlaid webs above a backsheet;
  f) disposing a topsheet above the stack of molded airlaid webs; and
  g) attaching the topsheet to the backsheet.

29. The method of claim 28, further comprising providing an outer absorbent member having a central void therein, the outer absorbent member being wider than the stack of molded airlaid webs, disposing a wicking barrier over the central void, and disposing the stack of molded airlaid webs over the central void such that at least a portion of the stack of molded airlaid webs resides within the central void, and wherein disposing the stack of molded airlaid webs above a backsheet comprises disposing the combination of the outer absorbent member, the wicking barrier, and the stack of molded airlaid webs above the backsheet.

30. The method of claim 28, further comprising providing at least one of the sections of airlaid webs with apertures.

31. The method of claim 28, wherein the three-dimensional shape of the molding surface for the first web differs from the shape of the molding surface for the second web.

32. The method of claim 28, wherein the three-dimensional shape of the molding surface for the first web is the same as the shape of the molding surface for the second web.

33. A method of making a molded absorbent article online in an automated machine, comprising:
  a) providing a continuous length of an airlaid web on a roll, the web comprising cellulosic fibers and thermoplastic binder material;
  b) conveying a the length of an airlaid web into an automated molding device comprising a molding substrate;
  c) heating the binder material in the airlaid web;
  d) deforming the airlaid web against the molding substrate to impose a shape to the airlaid web, wherein the shape comprises a central hump;
  e) removing the web from the molding substrate;
  f) allowing the thermoplastic binder material to cool;
  g) removing the airlaid web from the automated molding device; wherein the shape imposed by the molding substrate is stabilized in the finished absorbent article by the thermoplastic binder material, and;
  h) cutting the airlaid web to form a molded absorbent member; and
  I) attaching the molded absorbent member to a backsheet and a topsheet.

34. The method of claim 33, further comprising disposing one or more layers of additional absorbent material adjacent the airlaid web prior to disposing the airlaid web between a backsheet and a topsheet.

35. The method of claim 34, wherein at least one of the one or more layers of additional absorbent material comprise a molded airlaid web.

36. The method of claim 34, wherein at least one of the one or more layers of additional absorbent material comprise an absorbent foam.

37. The method of claim 33, wherein applying energy to the airlaid web comprises passing heated air through the web.

38. The method of claim 33, wherein the energy applied to the airlaid web comprises one of thermal energy, ultrasonic energy, radiofrequency energy, ultraviolet energy, electron beam energy, and infrared energy.

39. The method of claim 33, wherein the molding substrate is a rotating molding substrate and deforming the airlaid web against a the rotating molding substrate comprises applying vacuum pressure through the molding substrate.

40. The method of claim 33, wherein the molded absorbent member has longitudinal sides and wherein the shape imposed by the molding substrate further comprises a pair of raised longitudinal elements disposed between the central hump and the longitudinal sides of the molded absorbent member.

41. The method of claim 33, further comprising compressing a male embossing element against the airlaid web to form densified bending lines in the airlaid web as the airlaid web is being deformed against the molding substrate.

42. A method of preparing an absorbent article having an absorbent core with slotted gaps, comprising:
  a) providing a continuous length of an airlaid web on a roll, the web comprising cellulosic fibers and binder material;
  b) providing a portion of the airlaid web with a slit;
  c) conveying a the length of an airlaid web into an automated molding device comprising a molding substrate, such that the web is molded against the molding substrate, and wherein the molding substrate imposes a step change in height in the airlaid web about the slit;
  d) applying sufficient energy to the airlaid web to activate the binder material;
  e) removing the airlaid web from the automated molding device; wherein the shape imposed by the molding substrate is stabilized in the finished absorbent article by the binder material, and;
  f) cutting the airlaid web to form a molded absorbent member comprising the molded portion of the airlaid web; and
  g) attaching the molded absorbent member to a backsheet.

43. The method of claim 42, wherein the binder material comprises thermosetting material.

44. The method of claim 42, wherein the binder material comprises thermoplastic material.

45. The method of claim 42, wherein the applied energy is selected from microwave energy, ultraviolet energy, and heated air.

* * * * *

UNITED STATES PATENT AND TRADEMARK OFFICE
CERTIFICATE OF CORRECTION

PATENT NO. : 6,692,603 B1
DATED : February 17, 2004
INVENTOR(S) : Lindsay et al.

It is certified that error appears in the above-identified patent and that said Letters Patent is hereby corrected as shown below:

<u>Column 37,</u>
Line 60, delete "to"

<u>Column 38,</u>
Line 1, delete "section";
Line 21, delete "sections of";
Line 35, delete "a" which is between "conveying" and "the".

<u>Column 39,</u>
Line 5, delete "a" which is between "against" and "the";
Line 24, delete "a" which is between "conveying" and "the".

Signed and Sealed this

First Day of June, 2004

JON W. DUDAS
*Acting Director of the United States Patent and Trademark Office*